(12) United States Patent
Boggs et al.

(10) Patent No.: US 6,908,553 B1
(45) Date of Patent: *Jun. 21, 2005

(54) COMPOSITE MEMBRANE WITH PARTICULATE MATTER SUBSTANTIALLY IMMOBILIZED THEREIN

(75) Inventors: Daniel R. Boggs, Libertyville, IL (US); Shmuel Sternberg, Palatine, IL (US); Robin G. Pauley, Lake Villa, IL (US); Donna L. McLarty, Hoffman Estates, IL (US)

(73) Assignee: Baxter International Inc., Deerfield, IL (US)

(*) Notice: Subject to any disclaimer, the term of this patent is extended or adjusted under 35 U.S.C. 154(b) by 6 days.

This patent is subject to a terminal disclaimer.

(21) Appl. No.: 09/111,915

(22) Filed: Jul. 8, 1998

(51) Int. Cl.[7] ............................................ B01D 39/00
(52) U.S. Cl. ........................ 210/501.2; 210/500.27; 210/50.29; 210/500.36; 210/500.42; 210/490
(58) Field of Search ........................ 210/502.1, 500.27, 210/500.29, 500.36, 500.42, 490; 427/244, 245; 264/41

(56) References Cited

U.S. PATENT DOCUMENTS

| | | | |
|---|---|---|---|
| 3,158,532 A | * | 11/1964 | Pall ............................ 210/503 |
| 3,238,056 A | | 3/1966 | Pall, et al. |
| 3,746,175 A | * | 7/1973 | Markley |
| 3,908,044 A | | 9/1975 | Gunning |
| 3,996,131 A | | 12/1976 | Conn |
| 4,011,871 A | | 3/1977 | Taft |
| 4,384,954 A | * | 5/1983 | Nakashima et al. |
| 4,610,792 A | | 9/1986 | Van Gils et al. |
| 4,693,981 A | | 9/1987 | Wiesehahn et al. |
| 4,728,432 A | * | 3/1988 | Sugiyama et al. |
| 4,735,193 A | | 4/1988 | Kulprathipanja et al. |

(Continued)

FOREIGN PATENT DOCUMENTS

| | | |
|---|---|---|
| EP | 99 93 1933 | 12/2002 |
| WO | WO 91/08826 A1 | 6/1991 |
| WO | 97/07674 | 3/1997 |
| WO | 97/37536 | 10/1997 |
| WO | 98/30327 | 7/1998 |

OTHER PUBLICATIONS

PCT Written Opinion mailed Jul. 27, 2000 in PCT/US99/14471.
International Search Report for PCT/US99/14471, dated Sep. 13, 1999.*
Nakano, "Effects of Interaction with Surfactants, Adsorbents, and Other Substances on the Permeation of Chlorpromzaine through a Dimethyl Polysiloxane Membrane," *Journal of Pharmaceutical Sciences*, vol. 60, No. 4, pp. 571–575, Apr. 1971.
E. Denti et al., "Adsorption Characteristics of Cellulose Acetate Coated Charcoals," *J. Biomed. Mater. Res.*, vol. 9, pp. 143–140 (1975).

(Continued)

*Primary Examiner*—Ana Fortuna
(74) *Attorney, Agent, or Firm*—B. R. L. Price; J. P. Reagen; A. G. Kolomayets

(57) ABSTRACT

Membranes and methods for making membranes are disclosed. The membranes include a polymeric matrix and a particulate material immobilized within the matrix. The membranes may find particular application in methods and apparatus for removing organic compounds from a biological fluid as part of a pathogen inactivation treatment.

23 Claims, 15 Drawing Sheets

U.S. PATENT DOCUMENTS

| | | | |
|---|---|---|---|
| 4,748,120 A | | 5/1988 | Wiesehahn |
| 4,777,069 A | | 10/1988 | Cederberg et al. |
| 4,957,943 A | * | 9/1990 | McAllister et al. ............ 521/64 |
| 5,071,610 A | * | 12/1991 | Hagen et al. ................ 264/120 |
| 5,092,990 A | | 3/1992 | Muramatsu et al. |
| 5,102,547 A | | 4/1992 | Waite et al. |
| 5,197,208 A | | 3/1993 | Lapidus |
| 5,277,820 A | | 1/1994 | Ash |
| 5,312,576 A | | 5/1994 | Swei et al. |
| 5,472,607 A | * | 12/1995 | Mailvaganam et al. ..... 210/490 |
| 5,505,841 A | | 4/1996 | Pirbazari et al. |
| 5,559,250 A | | 9/1996 | Cook et al. |
| 5,639,376 A | | 6/1997 | Lee et al. |
| 5,660,731 A | | 8/1997 | Piechocki et al. |
| 5,660,903 A | * | 8/1997 | Andersen et al. |
| 5,691,132 A | | 11/1997 | Wollowitz et al. |
| 5,700,902 A | | 12/1997 | Hancock et al. |
| 5,714,521 A | * | 2/1998 | Kedem et al. |
| 5,795,483 A | | 8/1998 | Ung-Chhun et al. |
| 5,914,039 A | * | 6/1999 | Mahendran et al. ... 210/500.25 |
| 6,090,441 A | | 7/2000 | Vining, Jr. et al. |
| 6,099,734 A | | 8/2000 | Boggs et al. |
| 6,126,826 A | | 10/2000 | Pacheco et al. |
| 6,200,474 B1 | | 3/2001 | Kopaciewicz et al. |
| 6,513,666 B2 | | 2/2003 | Meyering et al. |

OTHER PUBLICATIONS

E. Denti et al., "Evaluation of novel sorbent systems for joint hemodialysis and hemoperfusion," *Medical Instrumentation*, vol. 11, No. 4, pp. 212–216, Jul.–Aug. 1977.

P.S. Malchesky et al., "Membranes Containing Sorbets for Blood Detoxification," vol. XXIII *Trans.Am.Soc.Artif.Intern. Organs*, pp. 659–665, 1977.

P.S. Malchesky et al., "Sorbent Membranes: Device Designs, Evaluations and Potential Applications," *Artificial Organs*, vol. 2, No. 4, pp. 367–371, Nov. 1978.

Tijssen et al., "A Hemoperfusion Column Based on Activated Carbon Granules Coated with an Ultrathin Membrane of Cellulose Acetate", *Artificial Organs*, vol. 3, No. 1, pp. 11–14, Feb., 1979.

L.B. Santamaria et al., *Rianimazione*, "L'emoperfusione mediante carbone attivato nel trattamento delle tossicopatie esogene acute," *Minerva Anestesiologica*, Min. Anest., 47, pp. 185–192, 1981.

Mori et al., "Permeability of heparinized hydrohilic polymer (H–RSD): Application to semipermeable membrane for microencapsulation of activated charcoal," *Journal of Biomedical Materials Research*, vol. 16, pp. 17–30, (1982).

Erhan Piskin et al., "The Past Present and Future of Artificial Organs," *International Symposium on Hemoperfusin and Artificial Organs*, 4th, Ankara, 1982.

Helen E. Kambic et al., "Historical Perspective Therapeutic Applications and New Frontiers," *The International Center for Artificial Organs and Transplantation*, Plasmapheresis (Brochure), Copyright 1983.

T.M.S. Chang et al., "Effect of Desferrioxamine on Removal of Aluminium and Iron by Coated Charcoal Haemoperfusion and Haemodialysis," *The Lancet*, pp. 1051–1053, Nov. 5, 1983.

Lopatikin et al., "Plasmapherese in der Komplexherapie bei Patienten mit akuter Pyelonephritis und Urosepsis," *Z. Urol. Nephrol.*, 79, pp. 317–324, (1986) H. 6.

Oka, "The Possibility of Improving Bioocompatibility by Removing Anaphylatoxins from the Circuit of Blood–Perfused Artifical Organs," vol. XXV *Trans Am Soc Artif Intern Organs*, pp. 778–783, 1989.

C.P. Ramos, M.D. et al., "Hemodialysis–Hemopefusion in Fulminant Viral Hepatitis," *Biomat., Art. Cells, Art. Org.*, 18(5), pp. 689–692, (1990).

E. Ben–Hur, "Inhibition of Phthalocyanine–Sensitized Photohemolysis of Human Erythroytes by Quercetin," *Photochemistry and Photobiology*, vol. 57, No. 6, pp. 984–988, 1993.

S. Rywkin et al., "New Phthalocyanines for Photodynamic Virus Inactivation in Red Blood Cell Concentrates," *Photochemsitry and Photobiology*, vol. 60, No. 2, pp. 165–170, 1994.

E. Ben Hur et al., "Virus inactivation in red cell concentrates by photosensitization with phthalocyanines: protection red cells but not of vesicular stomatitis virus with a water–soluble analogue of vitamin E," *Transfusion*, vol. 35, No. 5, pp. 401–406, 1995.

S. Rywkin et al., "Selective protection against IgG binding to red cells treated with phthalocyanines and red light for virus inactivation," *Transfusion*, vol. 35, No. 5, pp. 414–420, 1995.

H. Margolis–Nunno et al., "Elimination of potential mutagencity in platelet concentrates that are virally inactivated with psoralens and ultraviolet A light," *Transfusion*, vol. 35, No. 10, pp. 855–862, 1995.

Stephen J. Wagner et al., "Factors Affecting Virus Photoinactivation by a Series of Phenothiazine Dyes," *Photochemistry and Photobiology*, 67(3), pp. 343–349, 1998.

E. Ben–Hur et al., "Photodynamic decontamination of blood for transfusion," *New York Blood Center*.

"Measuring the Adsorption Capacity of Powdered Activated Carbon," *American Norit Company, Inc.,* Brochure.

"Preparation of natural essential oils free from psoralen cpds.—by contacting oils with water–insol. porous synthetic adsorbing resin e.g. spherical resin of polystyrene–polydivinyl benzene polymer," Abstract, AN 88–023972, JP 6228319B A (Hasegawa Co. Ltd. ) Dec. 9, 1987.

\* cited by examiner

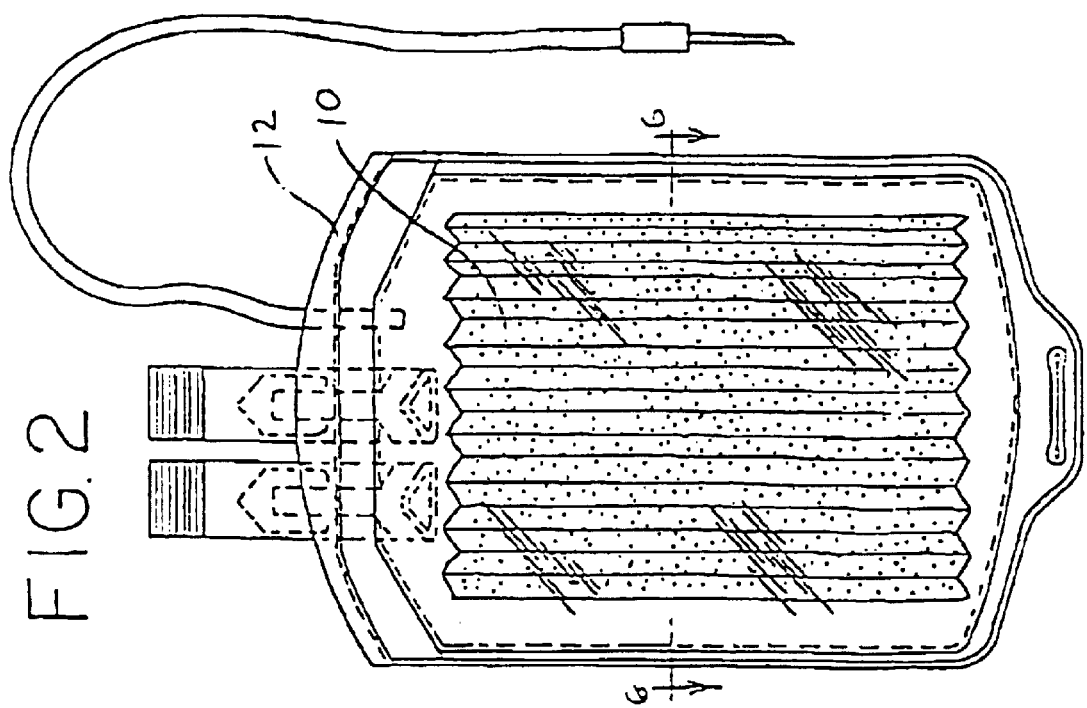
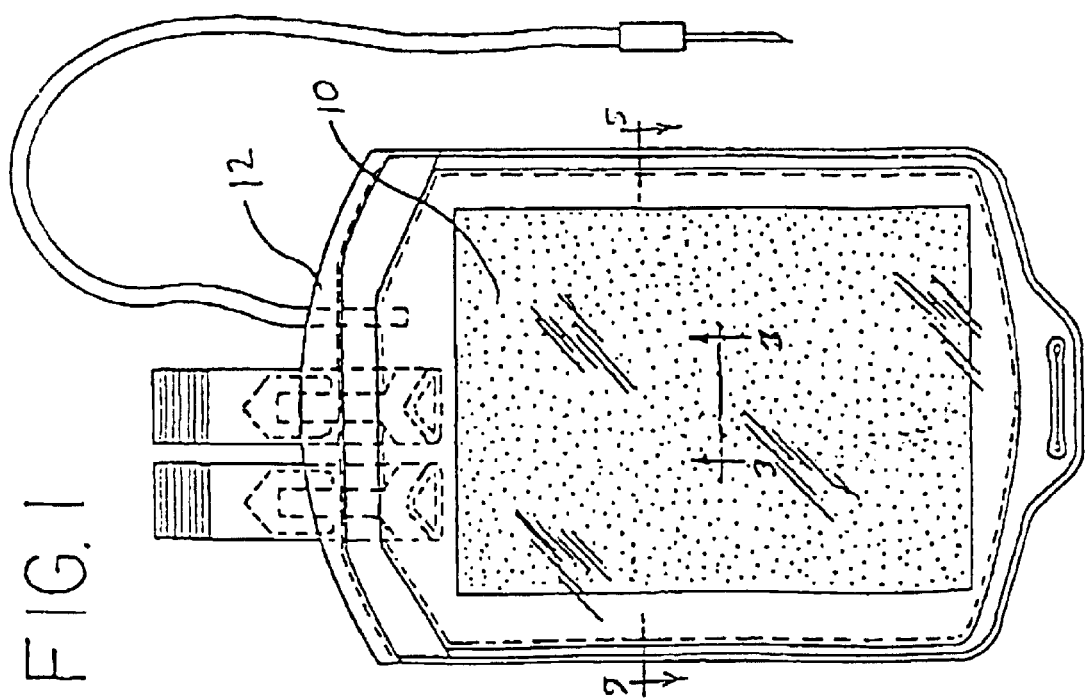

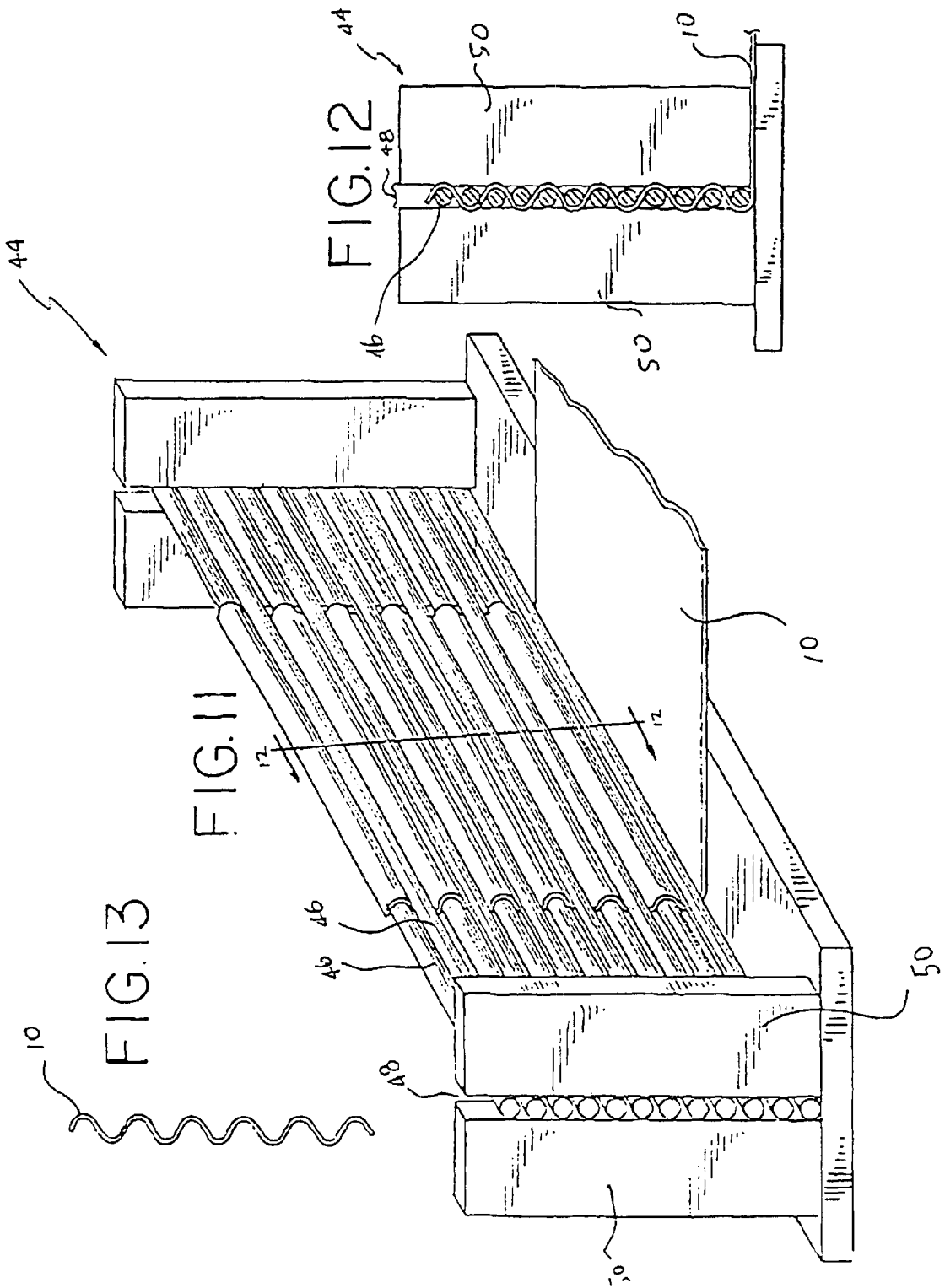

Levels of Acridine derivative in PRBC treated with 200 μM Acridine Compound and 2 mM GSH

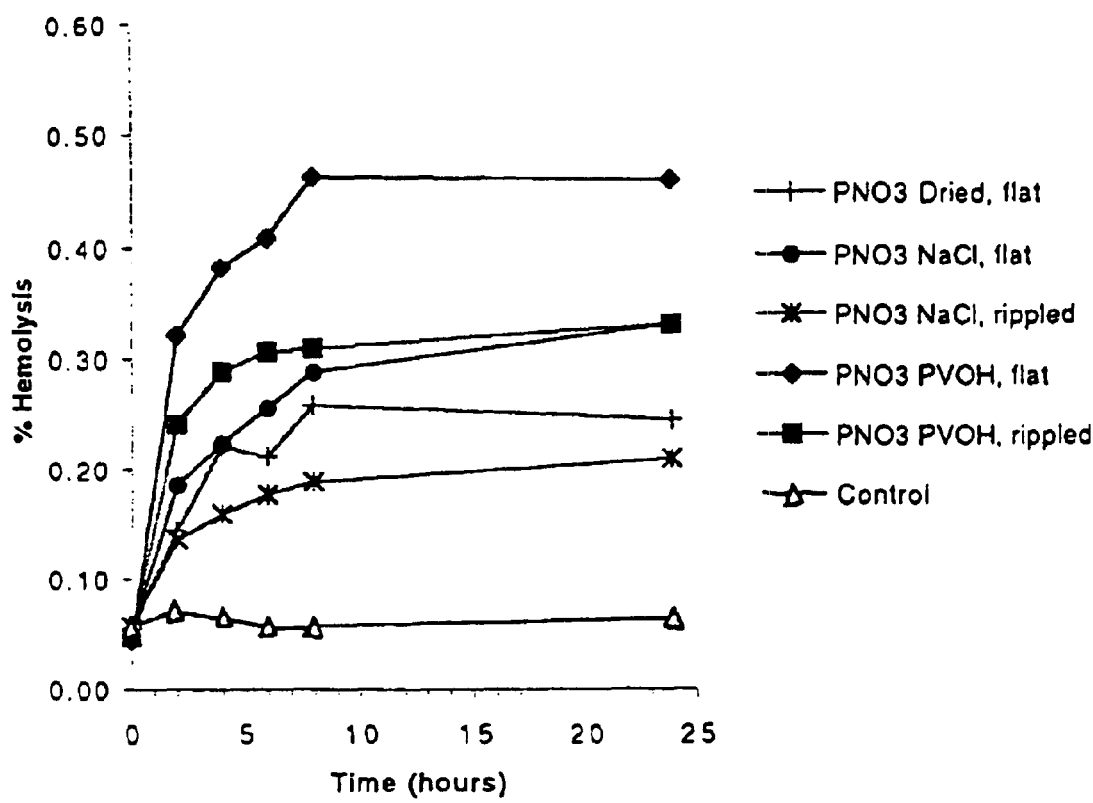

COMPOSITE MEMBRANE WITH PARTICULATE MATTER SUBSTANTIALLY IMMOBILIZED THEREIN

The present invention relates to composite membranes and to methods for making composite membranes. More particularly, the present invention relates to a novel composite membrane that includes a particulate material immobilized within a polymeric matrix and to a method for making such a membrane. The methods and apparatus employing such a membrane are particularly useful for removing organic compounds that have been added to a biological fluid, such as blood, as part of a pathogen inactivation treatment.

BACKGROUND OF THE INVENTION

Human blood includes both cellular and non-cellular components. The cellular components in blood include red blood cells (RBC), white blood cells (WBC), and platelets. Plasma is a non-cellular component of blood and is the liquid medium in which the cellular components are suspended. Plasma also includes various other components such as proteins, compounds that assist in blood coagulation (coagulation factors), electrolytes and metabolites.

During or after collection, human whole blood is commonly separated into its various components (RBC, WBC, platelets, plasma). Typically, the separated components may be stored for some period of time, and transfused to a patient in need of a particular blood component. For example, collected plasma may be transfused to a patient to provide plasma proteins and coagulation factors, or to replace lost blood volume. Platelets may be administered to cancer patients whose ability to produce platelets has been destroyed by chemotherapy and/or radiation treatment. RBCs may be administered to patients who have experienced rapid blood loss, or to improve the oxygen carrying capability of blood in patients suffering from anemia and the like.

It is now well known that viruses such as hepatitis B, hepatitis C, human immunodeficiency virus (HIV), cytomegalovirus and T-cell lymphotrophic virus (HTLV) may be resident within human blood and within the blood components. Certain bacteria such as *Yersinia enterocolitica* may also reside within human blood. The presence of virus and/or bacteria, (collectively referred to herein as "pathogens") in the blood stream poses the risk of infection and disease not only to the host, but also to a healthcare provider handling the blood, and/or if the collected blood or blood component is to be transfused, to the recipient of such blood or blood components. Accordingly, the medical community has attempted to reduce the risk of transfusing blood that contains such pathogens by developing methods and apparatus to remove or inactivate pathogens found in the blood component. AS used herein, "pathogen inactivation" (and forms thereof) means, generally, rendering a pathogen harmless to a living being. Pathogen inactivation includes killing, destroying, or eradicating a pathogen (either viral or bacterial), or either directly or indirectly inhibiting the ability of the pathogen to replicate. "Pathogen inactivating compounds" refers to compounds used in pathogen inactivation, including the decomposition products of such compounds.

One early attempt of removing virus from blood involved the filtration of blood and blood components to remove intracellular viruses entrained, for example, in white blood cells, Rawal et al., "Reduction of Human Immunodeficiency Virus-Infected Cells From Donor Blood by Leukocyte Filtration," *Transfusion*, pages 460–462 (1989).

Other prior methods for inactivating viruses and, in particular, extracellular viruses in blood, include steam sterilization of blood plasma and use of "detergents" to cleanse the blood or the blood component of the pathogens.

Pathogen inactivation has also been proposed by treating blood or blood components with a photochemical agent and light, referred to as "photoactivation". When activated by light of an appropriate wavelength, the photochemical agent either kills the virus directly or indirectly inhibits the ability of the virus to replicate and, thus, in either case "inactivates" the virus. Several known photochemical agents have been used or disclosed for use in inactivating viruses in blood, including psoralens, as described in U.S. Pat. No. 5,459,030; pthalocyanines, as described, for example in Rywkin, S. et al. Photochem. Photobiol. 60:165–170 (1994); and phenothiazine dyes, including without limitation, toluidine blue O, azure A, azure B, azure C, thionine, methylene blue and dimethylmethylene blue. For example, U.S. Pat. No. 5,527,704, incorporated by reference herein, discloses methods and apparatus for inactivating viruses in biological fluid in which a biological fluid (e.g., plasma) is combined with methylene blue and subjected, for a period of time, to light of a suitable intensity and wavelength for activating the methylene blue.

Other methods for treating biological fluid such as blood or blood components which do not involve photoactivation are also known. For example, International Publication No. WO98/070674 describes mustards linked to aziridines. U.S. Pat. Nos. 5,691,132 and 5,559,250 (which are incorporated by reference herein) describe methods for treating a biological fluid that includes RBCs by contacting the RBCs with a compound having a nucleic acid binding ligand and a mustard group. It is believed that such compounds react with nucleic acids of the pathogen (both viral and bacterial) to form covalent complexes that inhibit replication of the pathogen. Examples of acridine compounds include, but are not limited to, compounds such as N1, N1-bis (2-chloroethyl)-N4-(6-chloro-2-methoxy-9-acridinyl)-1,4 pentanediamine.

It may also be desirable to include certain other organic compounds in the above described treatment system to enhance the effectivity of the pathogen inactivating compound by reducing or "quenching" potential side reactions of the pathogen inactivating compound. For example, inclusion of certain naturally occurring tripeptides such as, but not limited to reduced L-glutathione quenches potential side reactions and allows for maximum pathogen inactivation by the pathogen inactivating compound. Other examples of quenchers useful in pathogen inactivation processes may include sulfydryls such as mercaptoethanol, as described in Rywkin, S. et al. *Transfusion* 35:414–20 (1995), cystein, quercitin, as described in Ben-Hur et al, Photochem. Photobiol 57:984–8 (1993) and rutin, as described in Margolis-Nunno, *Transfusion* 35:852–862 (1995).

As many of the pathogen inactivation methods known to date involve addition of either (1) compounds not normally present in blood (e.g., photochemical dyes, nucleic acid binding agents with mustard groups) or (2) concentrations of compounds (e.g., L-glutathione) in excess of typical concentrations found in human blood, it is desirable to remove substantially as much of the added compounds as possible from the treated biological fluid, prior to transfusion to a patient or other recipient.

For example, methods and devices for separating photoactive agents used in pathogen inactivation are described in U.S. Pat. No. 5,660,731. In that patent, photochemical agents such as methylene blue are separated from blood by contacting the photochemical agent with a porous medium that includes, for example, activated carbon fibers. The porous medium may be in the form of a web, sheet, cylinder or included in a filter with an inlet and outlet through which the biological fluid passes and, thus, contacts the porous medium.

A similar approach is described in U.S. Pat. No. 5,639,376 which discloses a filter for removing leukocytes and a viral inactivating agent such as methylene blue, its metabolites and photodecomposition products, from plasma or other blood fractions. As in U.S. Pat. No. 5,660,731, removal of the antiviral agent is achieved by contacting the blood with a filter adapted for removing, for example, both leukocytes and the antiviral agents. The filter includes activated carbon as a sorbent for methylene blue.

U.S. Pat. No. 4,728,432 more generally describes methods and devices for removing poisonous substances contained in blood by means of sorption. The sorbents described in that patent include, for example, activated carbon fixed to a support member. The activated carbon is combined with a polymer.

Other examples of methods and devices for removing organic compounds from a biological fluid are described in U.S. patent application Ser. No. 09/003,113, entitled "Methods and Devices for the Reduction of Small Organic Compounds from Blood Products" which is incorporated by reference herein. That application describes using sorbent particles such as activated carbon beads applied to a support for removal of, for example, acridine, acridine derivatives, methylene blue or thiols in a blood product. The activated carbon beads may be contained within a pouch or overwrap, or captured within a fiberized matrix, or captured within a fiberized matrix and contained within a pouch or overwrap.

SUMMARY OF INVENTION

The present invention is directed to a flexible composite membrane that includes a selected quantity of a polymeric compound and a selected quantity of a particulate material. The membrane includes a polymeric matrix with the particulate material substantially immobilized within the polymeric matrix. In accordance with one aspect of the present invention, the composite membrane includes a selectively permeable skin on the outer surface of the membrane.

In accordance with another aspect of the present invention, the flexible composite membrane includes a selected quantity of fine particles immobilized within the polymeric matrix where the majority of the particles have a diameter of less than about 20 $\mu$m. In accordance with another aspect of the present invention, the flexible composite membrane is contoured and includes a selected quantity of a non-fiberized polymeric material and a selected quantity of particulate material. The membrane includes a polymeric matrix and the particulate is substantially immobilized within the polymeric matrix.

In accordance with still another aspect of the present invention, the membrane includes a selected quantity of a polymeric material and a selected quantity of a particulate material. The membrane includes a polymeric matrix with the particulate material substantially immobilized within the polymeric matrix. The membrane has a thickness of at least about 400 $\mu$m.

The present invention is also directed to a method for making a flexible, composite membrane having a polymeric matrix and a particulate material immobilized by the polymeric matrix. The method may include, for example, providing a support having a first substantially flat surface and a second substantially flat surface. The method includes combining a polymer solution and a selected quantity of a particulate material to form a blend. A uniform thickness of the blend is applied to the surfaces of the support. In accordance with another aspect of the present invention, the membrane is treated with a wetting agent.

DESCRIPTION OF THE DRAWINGS

FIG. 1 is a perspective view of a container that includes a membrane embodying the present invention;

FIG. 2 is a perspective view of a container including an alternative embodiment of a membrane embodying the present invention;

FIG. 11 is a perspective view of an apparatus useful in the method of making membranes of the present invention;

FIG. 12 is a cross-sectional side view of the apparatus of FIG. 11 taken along 12—12;

FIG. 13 is a side view of another embodiment of a membrane made in accordance with the present invention;

FIG. 28 is a graph showing the percent hemolysis in packed RBC treated with an acridine compound and L-glutathione and contacted with a membrane made in accordance with the present invention.

DETAILED DESCRIPTION OF DRAWINGS

Turning now to the drawings, the present invention is shown, for purposes of illustration only, in connection with removal of pathogen inactivating compounds, including pathogen inactivating agents, their by-products and/or other added organic compounds employed in a pathogen inactivation process. As described more fully below, certain aspects of the present invention, such as the membrane and the method for making the membrane, have application beyond the field of pathogen inactivation of biological products. For example, the membrane and method for making it may have application in any other field or industry where it is desired to have an apparatus (such as membrane, tube, rod etc.) in which a particulate material is immobilized by or within a polymeric matrix. Accordingly, while the detailed written description of this invention is generally in the context of pathogen inactivation of biological fluids, such as blood components, the scope of the present invention is set forth in the appended claims.

Figure 6:
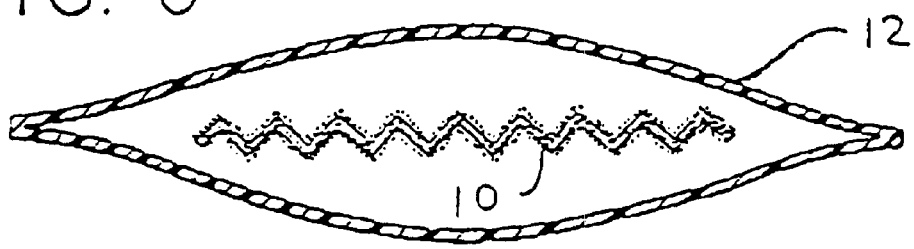
FIG. 6 is a side cross-sectional view of the container and membrane of FIG. 2 taken along 6—6.

FIG. 1 shows a membrane 10 made in accordance with the present invention inside a plastic container 12 suitable for holding a biological fluid, such as, but not limited to, blood and blood components. As shown in FIG. 1, membrane 10 may be in the shape of a flat sheet or, alternatively, pleated as shown in FIGS. 2 and 6 or rippled, as shown in FIG. 13. A pleated or rippled sheet enhances contact of the membrane surface with the compounds to be removed. Although the membranes 10 specifically shown in FIGS. 1 and 2, occupy much of the cross-sectional area of the container interior, it should be understood that the size and dimensions of the membrane sheet may be varied without departing from the present invention. Also, it will be understood that the present invention is not limited to sheet membranes (flat, pleated or rippled), but may also be embodied in other configurations such as fibers, rods, tubes and the like. Also, membranes made in accordance with the present invention may be housed in a device having a flow inlet and flow outlet. The device may include a substantially flat membrane where the flow of fluid is transverse to the membrane surface, or may include a rippled or pleated membrane whereby the areas between the ripples or pleats provide flow channels for axial flow of the fluid.

Turning briefly to a discussion of the container, container 12 may be made of any polymeric material that is typically used for making biomedical containers. For example, the container may be made of a polyvinyl chloride (PVC) that has been plasticized with a plasticizer such as DEHP, TEHTM, citrate ester or other known, biocompatible plasticizers. Alternatively, the container may be made of a non-PVC plastic, such polyolefin with or without a plasticizer. Examples of suitable biocompatible containers for storing biological fluid include the containers described in U.S. Pat. Nos. 5,167,657, 5,100,401 and 5,026,347.

Figure 3:
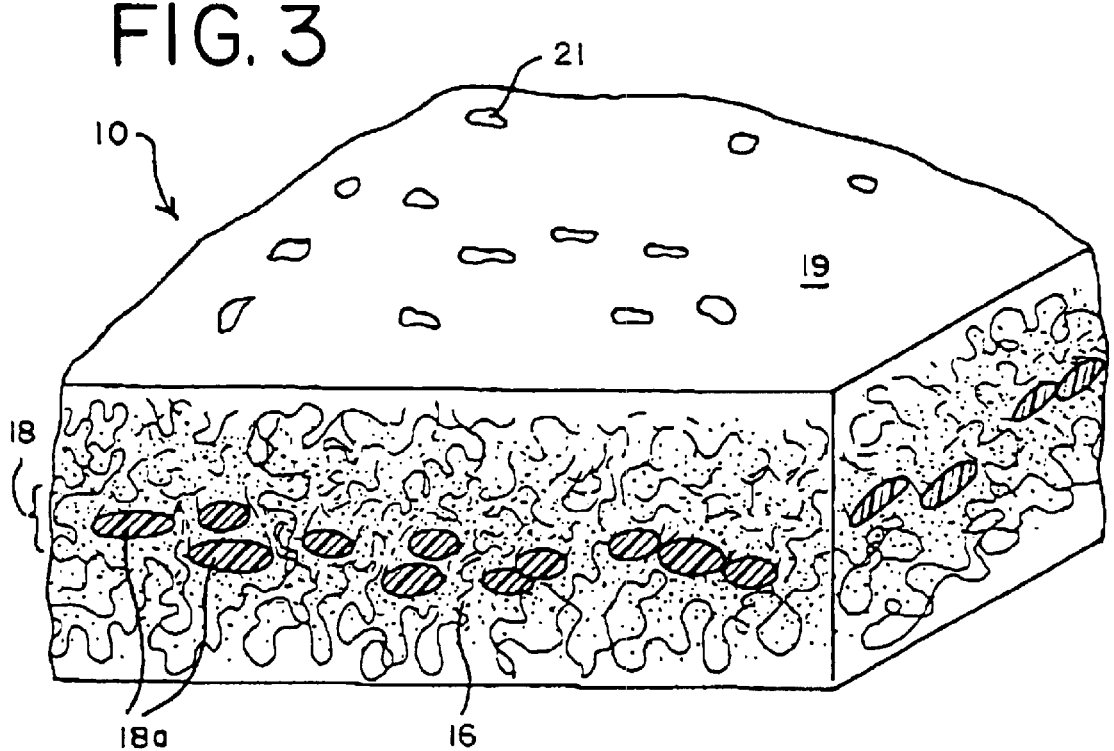
FIG. 3 is an enlarged, partial, side, cross-sectional view of a membrane (with a support) made in accordance with the present invention taken along 3—3 of FIG. 1.
Figure 4:
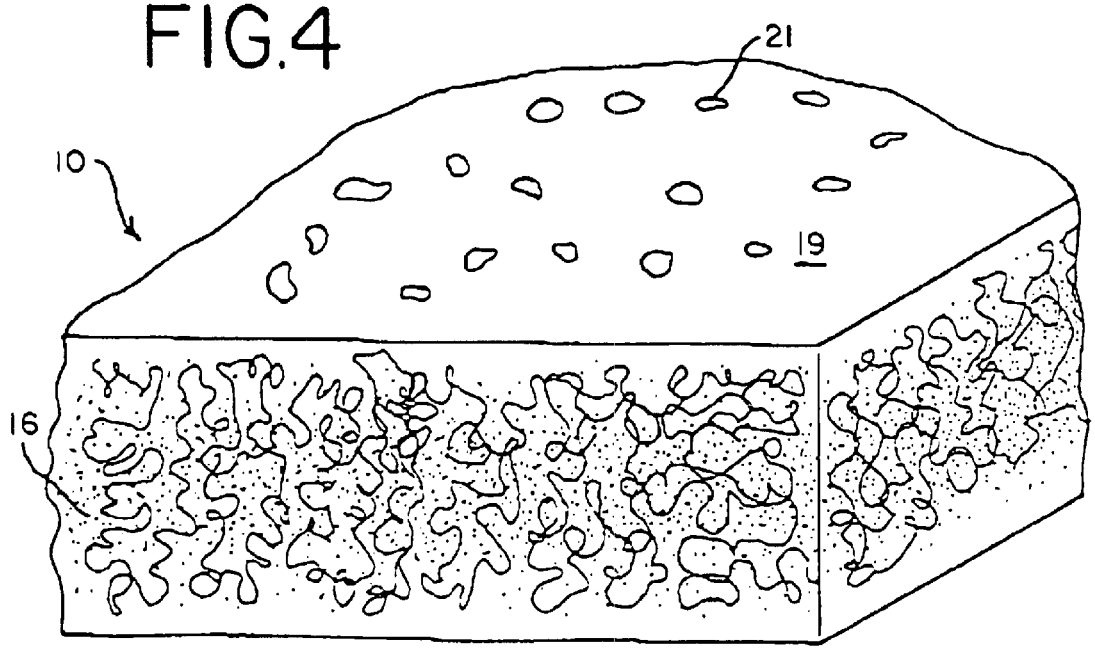
FIG. 4 is an enlarged, partial, side, cross-sectional view of a membrane (without a support) made in accordance with the present invention.
Figure 5:
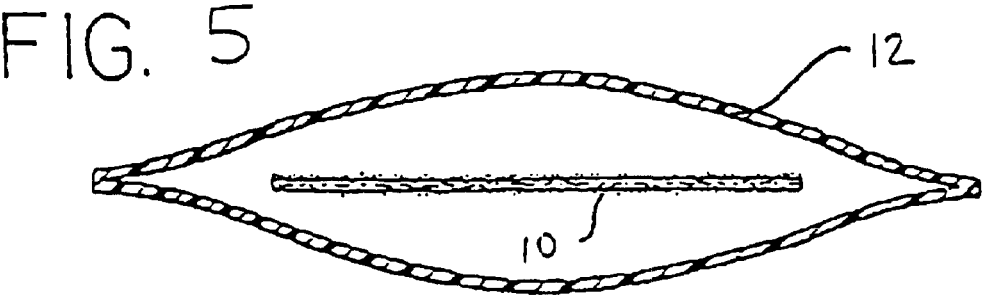
FIG. 5 is a side cross-sectional view of the container and membrane of FIG. 1 taken along 5—5.
Figure 7:
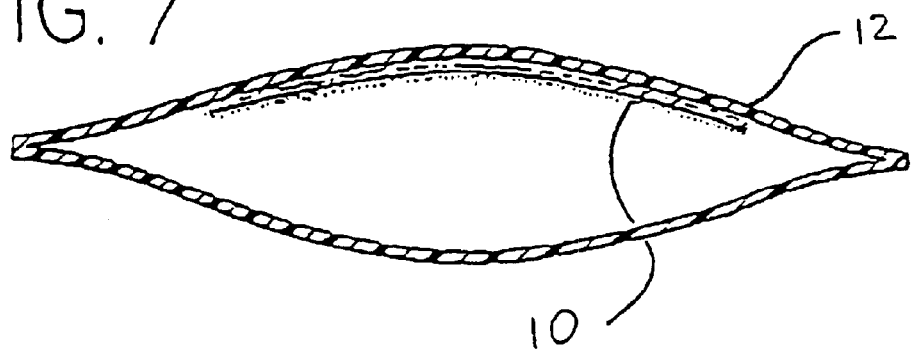
FIG. 7 is a side cross-sectional view of an alternative embodiment of the container and a membrane embodying the present invention.
Figure 7A:
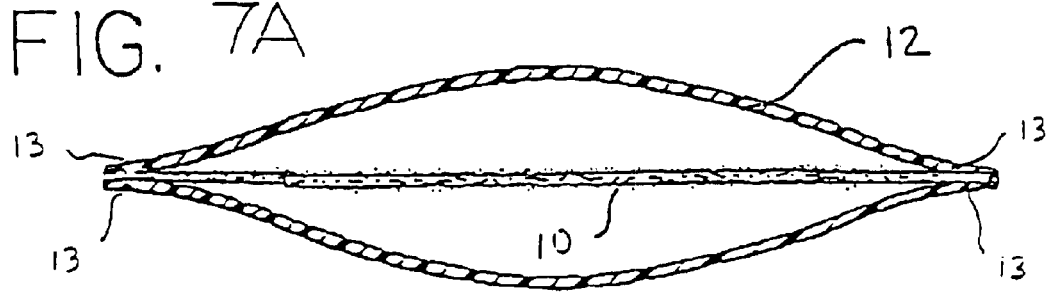
FIG. 7A is a side cross-sectional view of an alternative embodiment of the container and membrane embodying the present invention.

Returning now to a description of the membrane 10, as generally shown in FIGS. 3 and 4, membrane 10 is a composite of a polymeric material and a particulate material (shown as specs) within the polymeric matrix 16 of the membrane. Membrane 10 may optionally, include a support 18 (FIG. 3) or be made without a support (FIG. 4). As shown in FIG. 3, for example, support 18 forms the core of the membrane 10 and provides a substantially open structure within the continuous matrix 16 of the membrane. The outer surface of membrane 10 may further include a "skin" 19 (described in more detail below). As shown in FIG. 3 and in FIG. 18, the skin 19 may include randomly spaced surface pores 21. In another alternative, shown for example in FIG. 7, the membrane 10 may be supported directly by the interior of the container wall 12 (i.e., the container wall acting as a support). In still another alternative, the edges of membrane 10 may be held by the sealed walls 13 of container 12 as shown in FIG. 7A. Support 18 may be made of any material to which the polymeric material will adhere including, for example, polymers, glass, cloth or other fibrous material, (as shown, for example, in FIG. 3 wherein the fibers 18a may be seen). In one embodiment, the support may be a polyester mesh material. Such a material is available as Hollytex 3257 from Ahlstrom Corp. of Mount Holly Springs, Pa. As described above, membrane 10 may be made of a polymeric material (such as a polymer or copolymer) and a selected amount of a particulate material immobilized within the polymeric material. The polymeric material may be a polymer (including elastomers), a copolymer, mixtures of polymers, mixtures of copolymers or mixtures of polymers and copolymers. If membrane 10 is to be used in conjunction with a biological fluid, the polymeric material should not deleteriously affect the biological fluid which it contacts. The polymeric material should also be substantially miscible with the particulate material. Typically, the polymeric material may be hydrophilic, but may also be a hydrophobic polymeric material that is capable of being hydrophilized. Examples of polymeric materials suitable for use in the membrane of the present invention include, but are not limited to, polyurethane, cellulose acetate, polyvinylidene fluoride (PVDF) polyvinyl chloride (PVC), thermoplastic elastomers (such as those sold under the name Hytrel) and ethylene vinyl alcohol copolymer. Particularly useful in the present application are the polyurethanes. Polyurethanes are available from a variety of suppliers, such as Morton International Inc. The polyurethanes Morthane PNO3 and Morthane PB355, are presently preferred.

The particulate material should likewise be capable of being combined with the selected polymer. Where the membrane 10 is used to absorb selected organic compounds from a biological fluid, the particulate material may be a sorbent. Sorbents in powdered form may be preferred (over, for example, beads or other larger particles) so that the membrane will have a smoother surface and, thus, be less abrasive to the fluid which it contacts and the components therein. In addition, a powdered sorbent may be more effectively immobilized by the polymer. Of course, selection of the sorbent may also depend, in part, on the affinity of the compound to be removed for the particular sorbent.

Activated charcoal is a known sorbent and is the preferred sorbent for the present invention. Activated charcoal is available in bead form, however, for reasons set forth above, activated charcoal in a powdered form may be preferred. Activated charcoal is also available from a variety of sources. Examples of activated charcoal include activated charcoal powders available from Norit® Americas Inc. of Marshall, Tex. such as Norit Pac 200, Darco S51FF, Darco KB-B, Norit SX Ultra, G-60 Norit® A Supra, Norit® B Supra and Norit E® Supra. Typically, the particles of activated charcoal are porous and have a diameter of less than about 20 μm or even less than 10 μm and have a total surface area of greater than about 1000 m$^2$/g. Particularly useful in making the membranes of the present application is Norit® A Supra activated charcoal powder. For example, in Norit® A Supra, most of the particles have a diameter of less than about 20 μm and a substantial number have a diameter of less than about 10 μm. Norit® A Supra has typical total surface are of about 2000 m$^2$/g. Of course, other activated charcoals may also be used. Other examples of particulate materials suitable for use in the present invention include microporous polystyrene sorbent beads which, preferably, may be ground to provide smaller particles having a diameter of about 20 μm or less.

As discussed in more detail below, the above-described polymeric materials and particulate materials are combined to form a slurry-like blend used to make membrane 10. The blend includes (1) a polymer solution derived from a polymeric material dissolved in a solvent and (2) the particulate. Alternatively, the blend may include a molten polymer (i.e., no solvent) and particulate. As used herein, "blend" refers to the polymeric material (either as a polymer solution or molten polymer) and the particulate material. In accordance with the present invention, it is desirable that the amount of solids in the blend (i.e., excluding the solvent) include anywhere between about 40%–90%, by weight, of the particulate material and between about 10%–60%, by weight, of the polymeric material. In one embodiment, the amount of particulate (by weight) in the blend should be greater than 50% (of the solids). Preferably, the solids in the blend may include approximately 70% of the particulate material and approximately 30% of the polymeric material.

Figure 8:
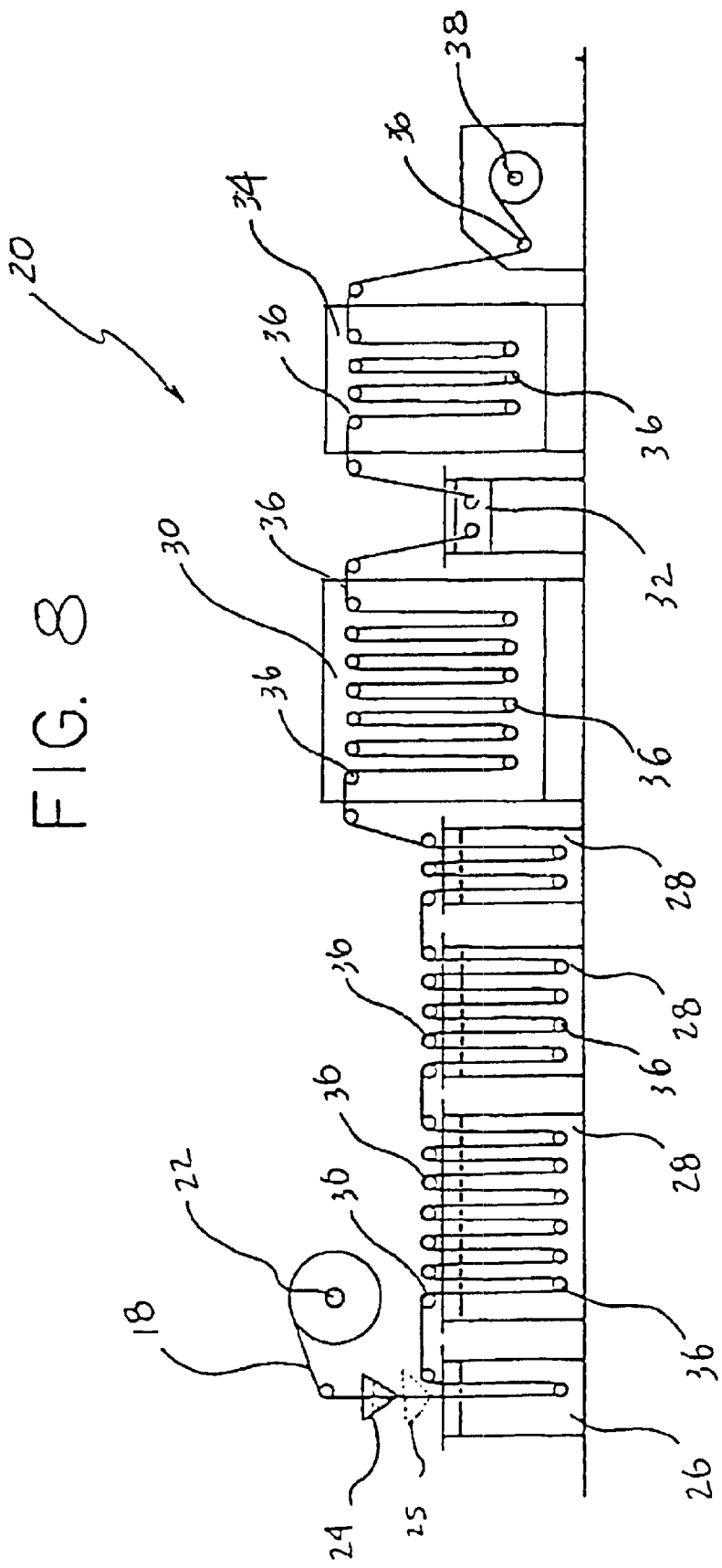
FIG. 8 is a diagram of the apparatus and method used for making membranes in accordance with the present invention.
Figure 9:
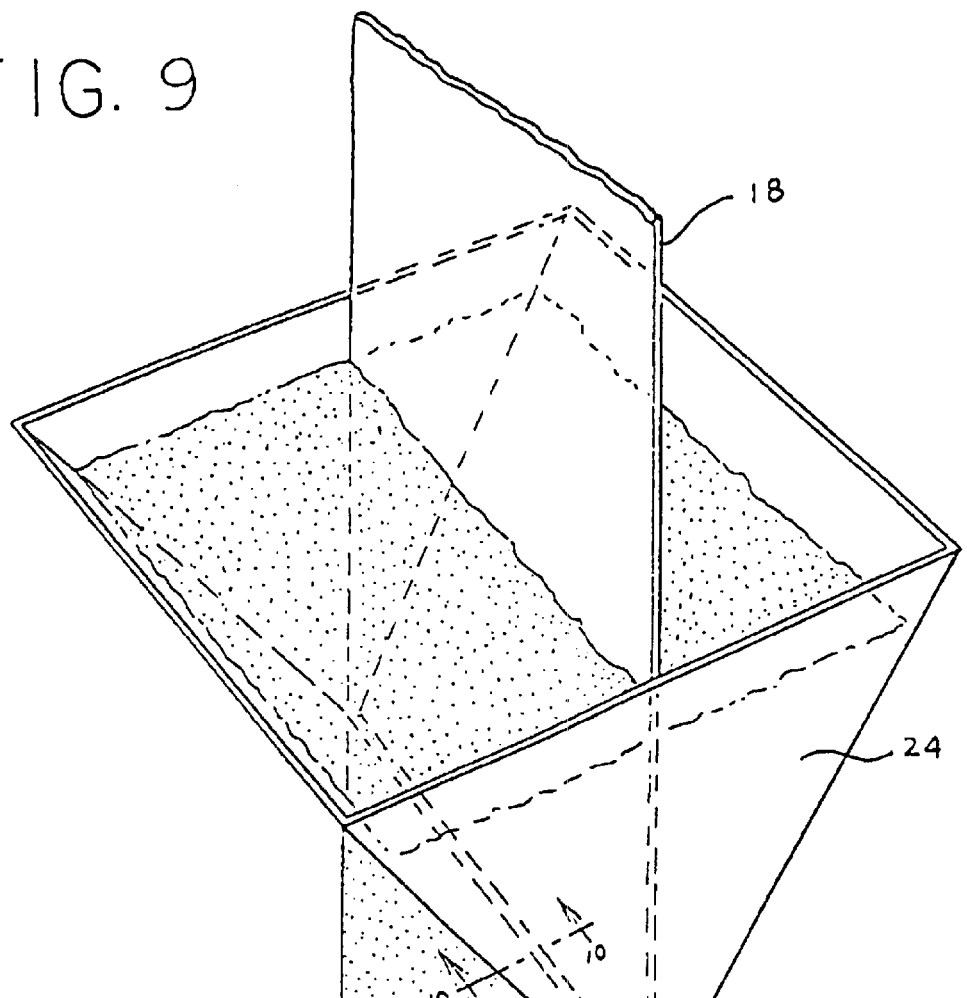
FIG. 9 is an enlarged perspective view of one stage of the apparatus and method shown in FIG. 8, in which a polymer solution/particulate blend is applied to a support.

Membranes of the type described above (and, in particular, those derived from a blend of a polymer solution and particulate) may be made, for example, by flow casting or extruding the blend onto a support 18 using the apparatus 20 generally depicted in FIG. 8. As shown in FIG. 8, apparatus 20 may include a rolled sheet of support 18. Support is dispensed (from dispenser 22) into a v-shaped chamber 24 that receives the sheet of support and the blend. The blend is applied to the outer surfaces of the support 18 (as shown in FIG. 9) within the chamber. The support with blend applied thereon exits the chamber through an opening at the bottom of the chamber 24. Of course, the membrane of the present invention may also be made without an integral support by, for example, applying the blend to a drum and, thereafter, peeling the membrane off the surface of the drum (and further processing the membrane as described below). In any event, whether the membrane 10 is made with or without a support, apparatus 20 may include one or more baths 26 and 28 containing solutions used in the process of making the membrane. Apparatus 20 also may include drying oven 30. Optionally, apparatus 20 may include additional bath 32 and oven 34 for further post-drying treatment of membrane 10. Typically, apparatus 20 includes a series of rollers 36 over which the membrane is threaded as generally shown in FIG. 8. Rotation of the rollers 36 effects movement of the membrane from dispenser 22, through the series of baths 26, 28, 32 and ovens 30 and 34. Finally, if desired, equipment for winding 38 and slitting the membrane 10 to its desired width may also be included.

In accordance with one method of making the membrane of the present invention, the polymeric material and the particulate material are combined in the proportions generally described above. Specifically, the polymeric material may first be dissolved in a suitable solvent. A variety of solvents may be used for different polymeric materials. For exemplary purposes only, where the polymer is a polyurethane or cellulose acetate, a suitable solvent may be N-methylpyrrolidone (NMP). A suitable solvent for PVC may be tetrahydrofuran, while a suitable solvent for PVDF may be dimethylacetamide (DMAC). Of course, it will be appreciated by those of skill in the art that other solvents may also be used.

A selected amount of the particulate material may then be added to the dissolved polymeric material (polymer solution) to provide the slurry-like blend. The blend is then introduced into chamber 24 through which support 18 has been threaded. As shown in more detail in FIGS. 9 and 10, chamber 24 is generally v-shaped and includes gap 40 at the bottom through which the support 18 exits. The width of gap 40 may be adjusted to accommodate different thicknesses of support 18 and also to control, in part, the thickness of the blend coated on support 18.

Figure 10:
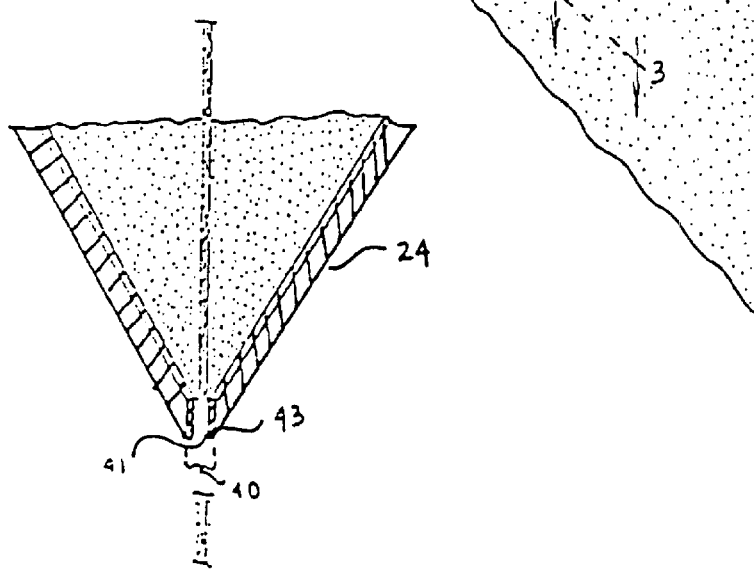
FIG. 10 is an enlarged cross-sectional side view of the apparatus of FIG. 9 taken along line 10—10 of FIG. 9.

As shown in FIG. 10, the lower portion of chamber 24 includes a narrow passageway 41 defined by downwardly extending walls (or land) 43. As the blend flows into the passageway 41, shear forces generated between the walls 43 and support 18 may urge the particles within the blend away from the walls 43 and toward the center of the membrane. Thus, it is presently believed that more of the particles may be distributed within the inner portions of the membrane than at or near the outer surfaces, (as generally shown, for example, in FIGS. 3 and 4) thus effectively providing the membrane with a "skin" portion over the interior of the membrane and, more specifically, the polymeric matrix. As more of the particles are disposed within the interior of the membrane than in or near the skin, it is less likely that particles will become dislodged from the membrane and enter the fluid with which membrane 10 is in contact during use. It is also believed that larger particles having, for example, a diameter greater than about 20 μm are excluded from entering passageway 41 and, therefore, are not included in the membrane. This may be desirable from the standpoint that larger particles may not be as effectively immobilized by or within the polymeric matrix. Thus, excluding larger particles decreases the possibility that particulate will become dislodged from the polymer and enter the fluid with which membrane 10 is in contact with during use.

In addition, walls 43 may also assist in providing that the thickness of the blend on either side of the support 18 is symmetric and uniform by ensuring that support 18 is properly centered within gap 40. It is believed that if support 18 is not properly centered within gap 40, the shear forces on either side of the support within passageway 41 will not be equal. The greater pressure on one side of the support 18 may shift the support back to the center of the gap 40. Thus, the apparatus of the present invention provides for a "self-centering" membrane that will receive a uniform coating of the blend. In one embodiment, the length of passageway, as defined by walls 43, may be between 0.5–3 cm in length.

In an alternative embodiment of the present invention, a second v-shaped chamber (shown in broken lines as chamber 25 in FIG. 8) may be used to apply an additional polymeric material to the membrane (to, for example, provide a protective coating and further prevent the particulate material near the surface of the membrane from becoming dislodged.) The second chamber may be placed in series with and below chamber 24, such that upon exiting chamber 24, support with the blend applied thereon enters the second chamber 25. The second chamber may, for example, include a different polymeric material or a more dilute concentration of the polymeric material used to make the blend, which may include a lower concentration of particulate material or no particulate material at all.

As shown in FIGS. 9 and 10, the blend may be applied to both sides of support 18. However, it will be understood that, optionally, only one side of the support 18 may be coated with the blend. In any event, the coated support is introduced into a first coagulation bath 26. Typically, in the first coagulation bath 26, the blend is contacted with a liquid or solution which is a non-solvent for the polymer portion of the polymeric solution, but is freely miscible with the solvent portion of the polymer solution. Contact with the liquid or solution coagulates the solids (polymer and particulate) and exchanges the liquid portion so that on exiting bath 26, the polymeric material/particulate blend includes two continuous but separated phases. One phase includes the polymeric material with embedded particulate and the other phase includes the non-solvent liquid.

Rotation of the rollers 36 advances the membrane 10 from coagulation bath 26 to one or more extraction baths 28. Typically, extraction baths 28 contain a solution that will extract from the membrane any residual solvent used to dissolve the polymer. Depending on the type and strength of solvent, the membrane may undergo a series of wash steps, each bath further washing and removing solvent from the membrane. For purposes of example only, three (3) extraction baths 28 are shown in FIG. 8.

Once the solvent has been substantially extracted from the membrane, the membrane may be dried. As shown in FIG. 8, after the final extraction bath, the membrane may be introduced into an oven 30 such as an air circulating oven. Of course, other forms of drying may also be used including air drying or contacting the membrane with a heated surface.

Prior to or after drying, the membrane 10 may be further treated with a surfactant or other agent to, for example, make the membrane 10 hydrophilic, prevent the loss of wettability (as a result of drying) or restore the wettability of the membrane which may have been lost or diminished as a result of drying. Thus, as shown in FIG. 8, the membrane may be introduced into another bath 32 containing the wetting agent or hydrophilizing coating agent. The method of applying the surfactant is not limited to immersing it in bath 32, but may also include spraying or other forms of applying the surfactant to the membrane. If treated with a treating agent, further drying in oven 34 may be desired. The membrane may then be cut (to its desired width) and wound up on apparatus 38. Membrane 10 may further be cut into smaller lengths for inclusion in a container 12. The edges of the cut membrane 10 may be enclosed or treated with an epoxy or other sealant.

As set forth above, the membrane may be further contoured into a pleated or rippled sheet. An apparatus 44 for forming a rippled membrane is shown in FIGS. 11–12 and the resultant membrane 10, is shown in FIG. 13. As shown in FIGS. 11–12, apparatus 44 may include a series of stacked rods 46, the ends of which are retained within slots 48 of support member 50. Membrane 10 is woven between rods 44 as substantially shown in FIG. 12. Apparatus 44 with woven membrane 10 is heat set for approximately 10–30 minutes at a temperature suitable for the polymer. For example, where the polymer is polyurethane, a typical temperature may be approximately 100° C. and a typical heating time may be approximately 15 minutes. After heating, the membrane retains a rippled shape as shown in FIG. 13. Of course, it will be appreciated that other ways of contouring (i.e., rippling, pleating) the membrane are also possible without departing from the present invention. The finished membrane 10 may then be sterilized by, for example, gamma radiation.

In a specific embodiment, membrane 10 is made of a polyurethane and activated charcoal powder. For example, polyurethane is dissolved in a solvent such as N-methylpyrrolidone (NMP). Between approximately 5%–20% by weight of polymer may be combined with approximately 80%–95% by weight of solvent to dissolve the polymer. Preferably, where the polymer is polyurethane the amount of polymer is between about 6%–15% of the total polymer/solvent weight. As used herein, the polymer solution is expressed as the percentage (in weight percent) of the polymer in the solvent. Thus, for example, 10 grams of polyurethane may be combined with 90 grams of NMP to provide a 10% polymer solution. The resulting polymer solution is then combined with the particulate material to form the blend.

As used herein, the composition of the blend is expressed as the weight percentage of a particulate material (such as activated charcoal) in the combined amount of particulate and polymer (the solids). Thus, for example, 10 grams of activated charcoal (or other particulate) added to the polymer solution that includes 10 grams of polymer and 90 grams of solvent, would provide a membrane having 50% charcoal and 50% polymer. Similarly, 30 grams of activated charcoal (particulate) added to a polymer solution having 10 grams of polymer (polyurethane) would result in a membrane having a 75% "loading" of activated charcoal (or other particulate) and 25% polyurethane (i.e., 30 grams of particulate in 40 (10–30) grams of polymer and particulate is a 75% loading of particulate). In any event, the amount of activated charcoal should be at least 10% by weight and preferably 70% by weight.

After blending the activated charcoal with the polymer solution, the blend is then introduced into the chamber 24 as described above and may be applied to a polyester mesh material supplied from dispensing roll 22. In a preferred embodiment, the blend is applied to both sides of the polyester support, as shown in FIGS. 9 and 10, to achieve a total membrane thickness (film and support), 44, of approximately between 250 and 1000 micrometers ($\mu$) and, preferably, 400–1000 micrometers. It has been observed that to achieve a membrane thickness of approximately 400–1000 micrometers ($\mu$), gap 40 in chamber 24 should be slightly wider than the desired thickness of the membrane and may measure, for example, between about 600–1200 micrometers. More specifically, it has been observed that to provide a polyurethane membrane with 70% activated charcoal powder having a thickness of about 500 µm, gap 40 should be approximately 705 µm, and to provide a polyurethane membrane with 70% activated charcoal powder having a thickness of 1000 µm, gap 40 should be approximately 1105 µm. The membrane 10 is then introduced into coagulation bath 26 which, in the case of the polyurethane/activated charcoal blend described above, may include only water. As presently understood, exposure of the blend to water causes the polymeric blend to coagulate (because polyurethane is not miscible with water). As coagulation of the polymer proceeds, solvent NMP leaves the polymer in exchange for water. Further removal of solvent from the membrane occurs as the membrane is successively introduced to and removed from a series of extraction baths 28.

The rate of movement of the membrane 10 through the coagulation 26 bath, extraction baths 28 and ovens 30 and 34 may be controlled (by, for example, a human operator) by adjusting the rate of rotation of the rollers 30. For example, in one embodiment where the membrane includes 70% activated charcoal in a 10% polyurethane solution, the membrane advances through the coagulation, extraction baths and drying ovens at approximately between 1–4 ft/min and, typically 1 ft/min. This ensures, for example, that the solvent (NMP) is substantially extracted from the membrane, results in a thickness of the membrane that is within the preferred range, provides for sufficient drying and ensures that membrane is sufficiently treated with surfactant, if such treatment is desired. Of course, for polymers other than polyurethane, different solutions for coagulation/extraction, different line speeds to either shorten or lengthen the residence time of the membrane in the coagulation and extraction baths may be desirable or even required. For example, if the polymer is PVDF, the coagulation bath may include methanol.

After extraction of the NMP solvent, membrane 10 may be dried in oven 30 for anywhere between 10 and 30 minutes at a temperature of at least 40° C. and typically 50° C.

Membrane 10 may be treated with a wetting agent or hydrophilizing coating agent (hereinafter "treating agent") in bath 32 to enhance the sorption characteristics of membrane 10, prevent the loss of wettability after drying or restore lost or diminished wettability of the membrane caused by drying. The treating agent may be a compound (dissolved in an appropriate solvent) that is capable of hydrophilizing the membrane 10. For example, the treating agent may be polyvinyl alcohol (PVOH) dissolved in an isopropyl alcohol/water solution. Specifically, where the polymer is made of polyurethane with activated charcoal, the hydrophilizing bath may include between approximately 0.20%–0.5% PVOH in an approximately 50/50 water/isopropyl alcohol solution. For membranes made of polyurethane and activated charcoal, 0.25% up to about 1% PVOH solutions may be preferred.

Other solutions may also be used to treat the membrane 10 and make it more hydrophilic. Specifically, solutions including sodium chloride are suitable, including solutions that include 0.45% NaCl or 0.9% NaCl. This may include, for example, solutions commonly used in the storage of red blood cells, such as Adsol® (described in U.S. Pat. No. 4,267,269 incorporated by reference herein). Still other solutions that may be used to treat the membrane include 1–10% glycerol in isopropyl alcohol, polyethylene oxide (PEO) and/or blends of PEO and polyurethane in 70/30, 50/50, 30/70, isopropyl alcohol/water solutions. Where the membrane is used with a biological fluid, such as blood, membrane 10 may also be treated with an agent that further improves the hemocompatability of the membrane relative to retain compounds or biological components. One such agent is polyhydroxyethylmethacrylate or pHEMA. In any event, the membrane 10 may be treated with the above described solutions prior to or after drying.

Membranes made in accordance with the present invention provide a unique and cost effective way of immobilizing fine particulate powder that is typically difficult to handle and prone to shedding. This is particularly advantageous in the field of blood therapy where introducing foreign particles into the blood or other biological fluid is considered undesirable. The membranes made in accordance with the present invention are also unique, in part, because the particulate is substantially captured by the polymer matrix without compromising the ability of the powder to act as a sorbent for organic compounds used in pathogen inactivation treatments. As presently understood, the fine powder is widely dispersed across the polymeric matrix and, therefore, provides a multitude of sorption sites for the molecules of the organic compounds. The broad dispersal of powder may also mean that molecules of the organic compounds will have to travel shorter distances before they are captured by the sorbent powder.

Actual membranes made in accordance with the present invention are shown in FIGS. 14–20. In particular, FIGS. 14–20 show a membrane made from a blend derived from a 10% polyurethane solution (PNO3) to which was added Norit® A Supra activated charcoal powder to obtain a charcoal loading of approximately 70% (i.e., the solids comprise 70% activated charcoal and 30% polyurethane). The membrane was prepared using the apparatus generally depicted in FIG. 8 (using a single chamber 24) and described herein. A polyester mesh was used as a support.

Figure 14:
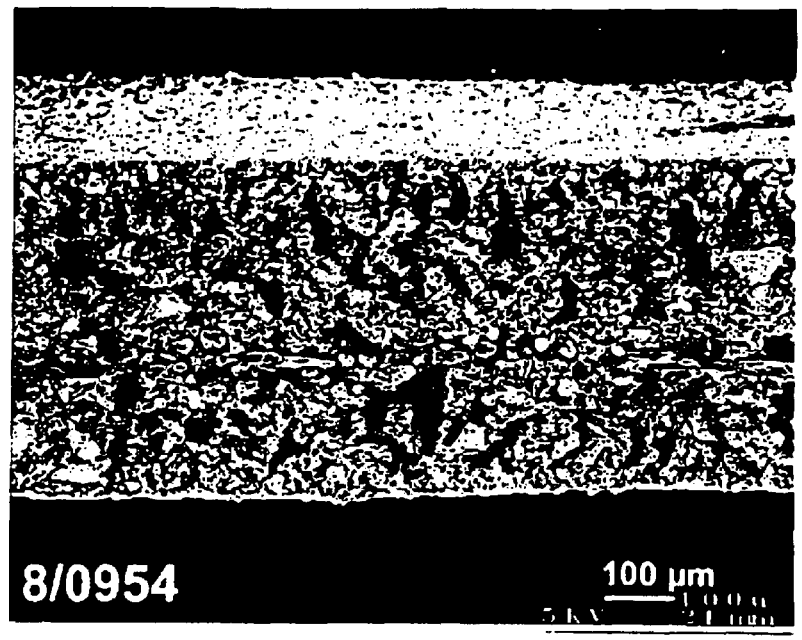
FIG. 14 is a photograph of a cross-sectional view of an actual membrane (magnified approximately 100×) embodying the present invention, using a scanning electron microscope.
Figure 15:
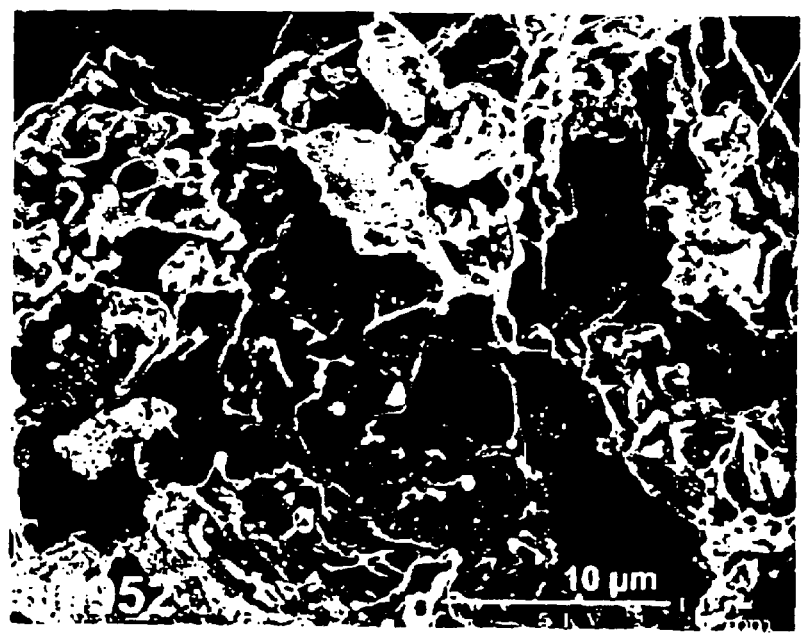
FIG. 15 is a photograph of a cross-sectional view of an actual membrane (magnified approximately 3300×) embodying the present invention, using a scanning electron microscope.
Figure 16:
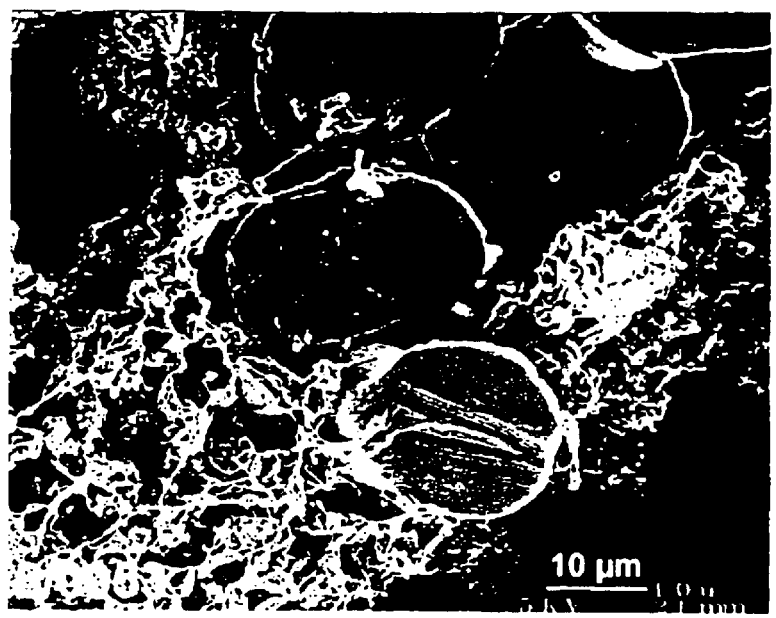
FIG. 16 is a photograph of a cross-sectional view of an actual membrane (magnified approximately 1500×) embodying the present invention, taken near the support, using a scanning electron microscope.
Figure 17:
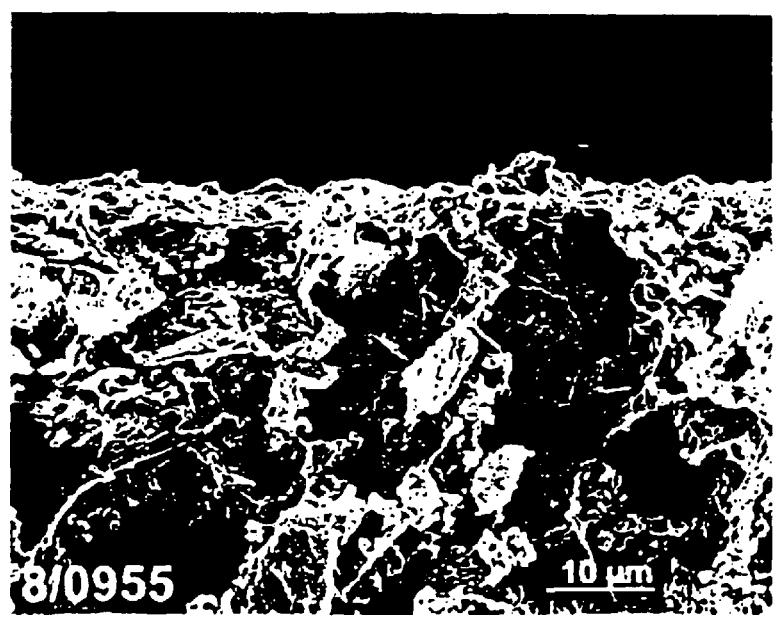
FIG. 17 is a photograph of a cross-sectional view of an actual membrane (magnified approximately 1600×) embodying the present invention, taken near the outer surface of the membrane, using a scanning electron microscope.

The resultant membrane includes a polymeric matrix which, in FIG. 14, appears as an array of sponge-like structures. As further seen in FIG. 14, the polymeric matrix is substantially continuous throughout the membrane, even across portions of the polyester mesh support. The polyester mesh support is seen, in cross section, as the larger circular or oval structures near the center of the membrane. The top and bottom surfaces of the polymeric matrix include a thin "skin" layer. As seen in FIGS. 15–17, it is believed that the semi-spherical, grain-like bodies may be particles of activated charcoal immobilized within the polymeric matrix.

Figure 18:
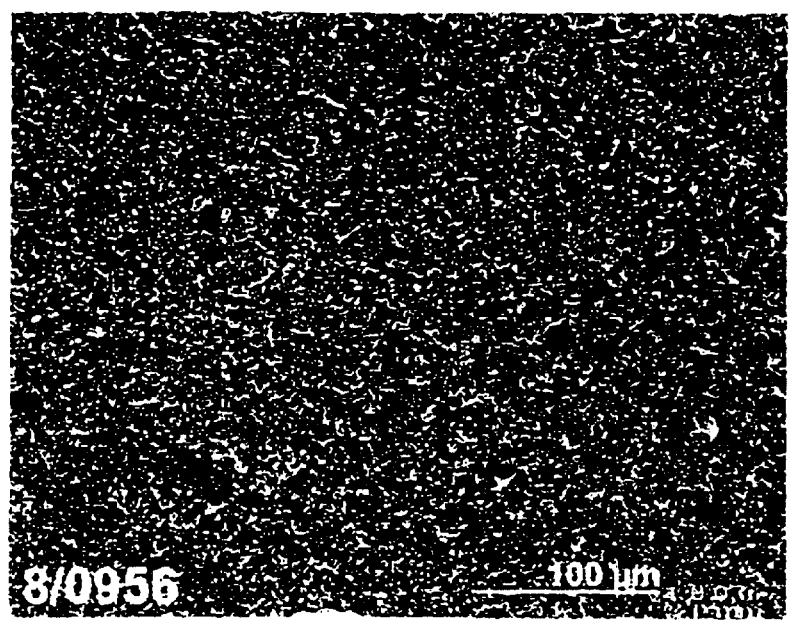
FIG. 18 is a photograph of the surface of an actual membrane (magnified approximately 270×) embodying the present invention, using a scanning electron microscope.
Figure 19:
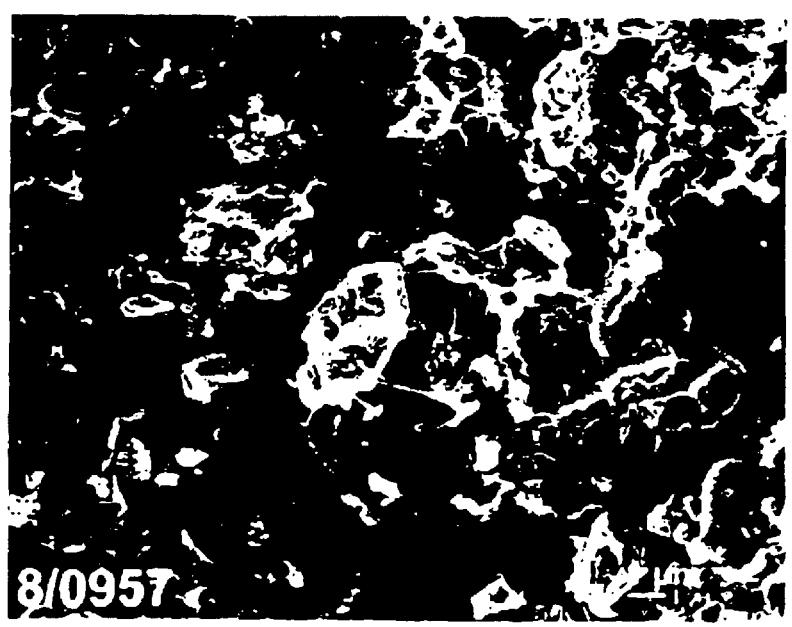
FIG. 19 is a photograph of the surface of an actual membrane (magnified approximately 5500×) embodying the present invention, using a scanning electron microscope
Figure 20:
FIG. 20 is a photograph of the surface of an actual membrane (magnified approximately 37,000×) embodying the present invention, using a scanning electron microscope
Figure 21:
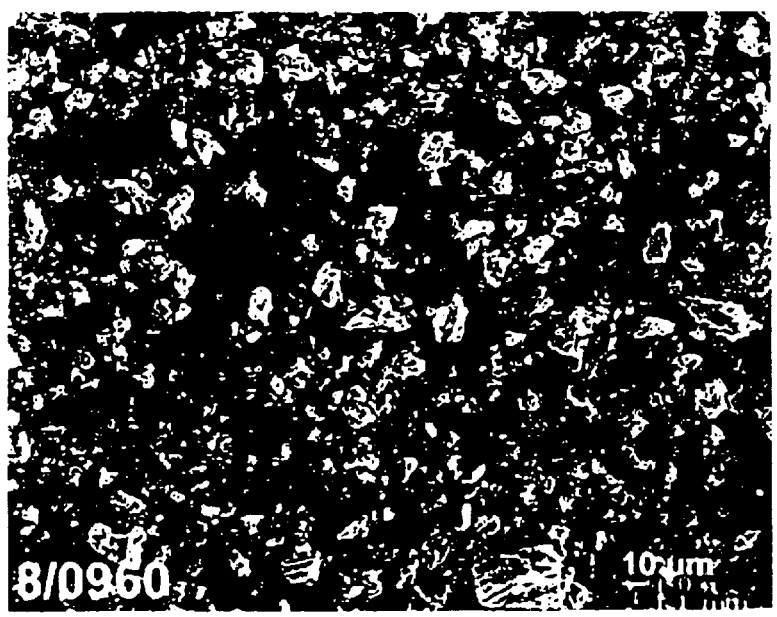
FIG. 21 is a photograph of activated charcoal powder particles (magnified approximately 400×), using a scanning electron microscope.
Figure 22:
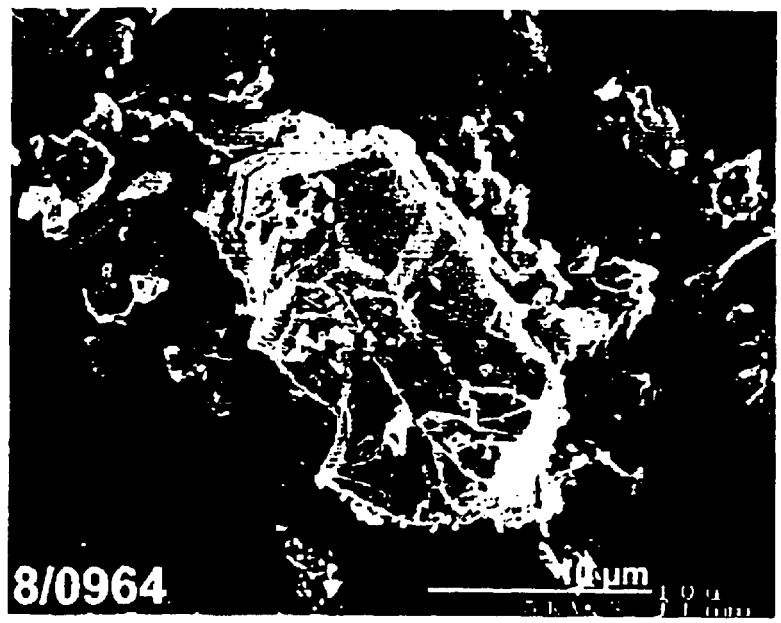
FIG. 22 is a photograph of activated charcoal powder particles (magnified approximately 3300×) using a scanning electron microscope.
Figure 23:
FIG. 23 is a photograph of activated charcoal powder particles (magnified approximately 37,000×) using a scanning electron microscope.

FIG. 18 is a photograph of the surface of the membrane and, more particularly, the skin. As seen in FIGS. 18 and 19, the skin is not completely continuous, but includes randomly spaced voids across the membrane. When magnified, charcoal particles held by the polymeric material near the surface of the membrane may be seen (FIGS. 19 and 20). As seen in FIG. 20, the activated charcoal particle coated with the polymeric material has a textured look, not seen in the photographs of the activated charcoal particles alone (FIGS. 22–23). It is believed that the skin layer of the polymeric matrix assists in preventing the particles from dislodging. Significantly, while providing this protective function, the skin layer does not interfere with mass transport and remains permeable to certain molecules of the organic compounds to be removed. When used in pathogen inactivation processes, the membrane skin is permeable to certain pathogen inactivation compounds but not, for example, to cellular or other components found in blood.

To test the effectiveness of the membranes of the present invention, samples of prepared membranes were contacted with solutions containing various compounds commonly used in pathogen inactivation procedures. The test procedures and results are described below.

Membranes of polyurethane and activated charcoal were prepared as substantially described above. The polyurethane/activated charcoal blend included 10% of the polyurethane PNO3 combined with 90% NMP solvent. Activated charcoal was added to obtain an activated charcoal loading of 70%. The blend was applied to a polyester mesh support as substantially described above to form a membrane. Two membranes were dried and treated with either 1) 0.25% PVOH in a 50/50 water/isopropyl alcohol solution or 2) 0.9% NaCl solution. Other membranes served as controls and were either dried only (and not treated with any solution) or not dried at all.

EXAMPLE 1

Figure 24:
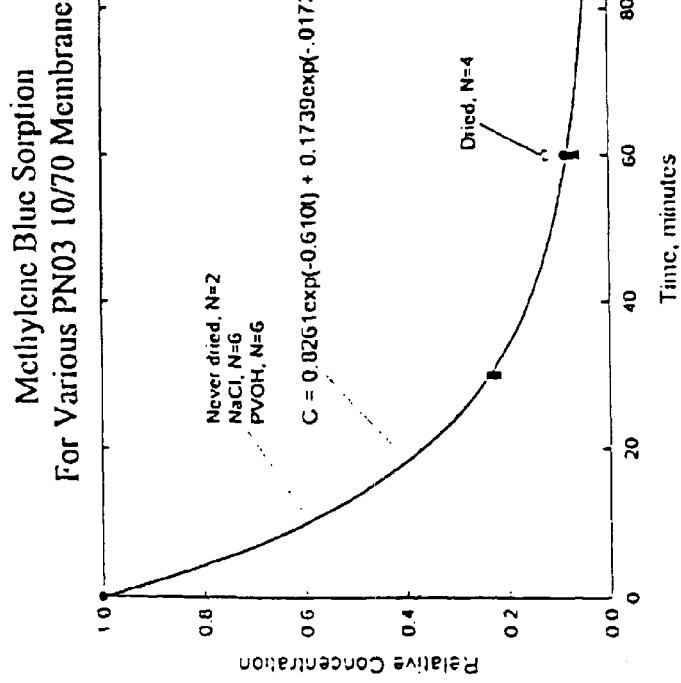
FIG. 24 is a graph showing the rate of sorption of methylene blue by a membrane made in accordance with the present invention.

A solution containing 50 μm methylene blue phosphate buffered saline was prepared and distributed into test tubes. Samples of the membranes prepared as described above were placed in each test tube. The ratio of membrane surface to fluid was approximately 2.0 $cm^2$/ml. Samples were then taken from the test tubes at timed intervals. The degree of sorption of methylene blue was measured by spectroscopic means (at 630 nm). The results are shown in FIG. 24.

EXAMPLE 2

Figure 25:
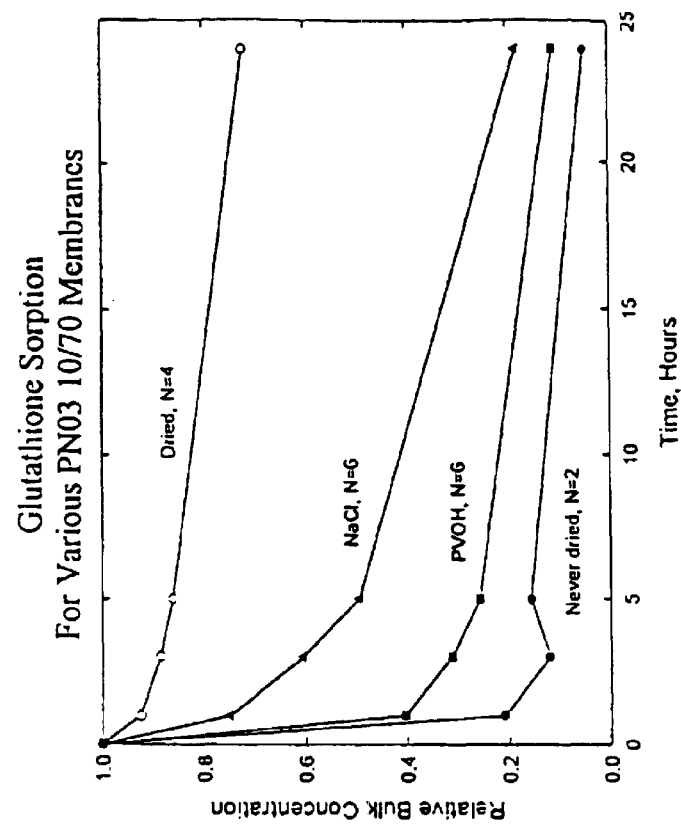
FIG. 25 is a graph showing the rate of sorption of L-glutathione by a membrane made in accordance with the present invention.

A solution containing 6 mM reduced L-glutathione in phosphate buffered saline was prepared and distributed into test tubes. Samples of the membranes prepared as described above were placed in each test tube. The ratio of membrane surface to fluid was approximately 2.0 $cm^2$/ml. Samples were then taken from the test tubes at timed intervals and the degree of sorption was determined by high performance liquid chromatography (HPLC). The results are shown in FIG. 25.

EXAMPLE 3

A membrane, having a 70% loading of activated charcoal in a 10% polyurethane (PNO3) solution was prepared as substantially described above. The membrane was cut into two 22.7×10.7 $cm^2$ sheets and placed inside of two separate 1 liter blood bags. Two units (approximately 300 ml each) of packed RBC were prepared by standard blood banking procedures and the acridine derivative (5-[β-carboxyethyl) amino} acridine (abbreviated as AD) of Example 3 and L-glutathione were added to each of the units. The starting concentrations of the acridine derivative and L-glutathione were measured and are reported below in Table 1 below (Time 0). Each unit of packed RBC was transferred to a container, including the sample membrane (described above). The ratio of membrane surface to fluid was approximately 2.5 $cm^2$/ml The containers were placed on a orbital shaker and agitated at room temperature. Samples were removed at 1, 4 and 24 hours for analysis. The packed RBC samples were centrifuged in a microfuge at maximum RPM and the plasma supernatants were transferred to separate vials for analysis of L-glutathione (GSH) and acridine derivative by HPLC. Samples of packed RBCs were also analyzed with a Sysmex cell counter to determine the degree of hemolysis in the various samples. The results are summarized in Table 1 below.

TABLE 1

| Sample Time | AD (μM) | GSH (mM) | % Hemolysis |
|---|---|---|---|
| Time 0 | 584.02 | 6.75 | 1.95 |
| 1 Hour | 124.72 | 5.77 | 2.05 |
| 4 Hour | 6.07 | 4.88 | 1.95 |
| 24 Hour | 1.15 | 3.85 | 2.25 |

As shown from these examples, a ratio of membrane surface to fluid of between about 2.0 $cm^2$/ml –2.5 $cm^2$/ml is effective for reducing the concentrations of pathogen inactivating compounds. Such ratios are particularly effective for the embodiments shown in FIGS. 1 and 2. (i.e., a membrane sheet within a container of biological fluid), although any ratios of between 1.0–5.0 $cm^2$/ml may also be effective for removing pathogen inactivating compounds in these or other embodiments.

EXAMPLE 4

The ability of five (5) different membranes, all made in accordance with the present invention, to remove pathogen inactivating treating agents, from packed red blood cells was also evaluated. The membranes evaluated included a 70% loading of activated charcoal in a 10% polyurethane (PNO3) solution (as defined above). The sample membranes were, in some cases (e.g., test articles 2–5), treated with a treating agent and configured (flat or rippled) as set forth below. For comparison, test article 6 (a control) was a container of packed and treated (as described below) RBCs that included no sorbent whatsoever.

TABLE 2

SAMPLE MEMBRANES

| Test Article | Membrane Treatment & Configuration |
|---|---|
| 1 | No treatment & dried, flat |
| 2 | 0.9% NaCl & dried, flat |
| 3 | 0.9% NaCl & dried, rippled |
| 4 | 0.25% PVOH & dried, flat |
| 5 | 0.25% PVOH & dried, rippled |
| 6 | No sorbent (control) |

Seven units of ABO matched whole blood were obtained. Each unit was centrifuged at 5,000×G for five minutes in a Sorval RC-3B centrifuge at 4150 rpm. The supernatant plasma was expressed and 94 ml of a solution that included approximately 25 mM sodium citrate dihydrate, 4.4 mm sodium acid phosphate dihydrate, 16 mM of sodium phosphate dihydrate, 1.5 mM adenine and 39.9 mM of mannitol having a pH of approximately 7.3 was added to each unit. The packed red blood cells were than pooled in a three liter container. The measured hematocrit was 64%. The packed RBC were then dispensed into seven separate containers, each container including approximately 280 ml of packed red blood cells. The packed red blood cells were than dispensed into plastic containers and held at 4° C. for approximately four hours.

Figure 26:
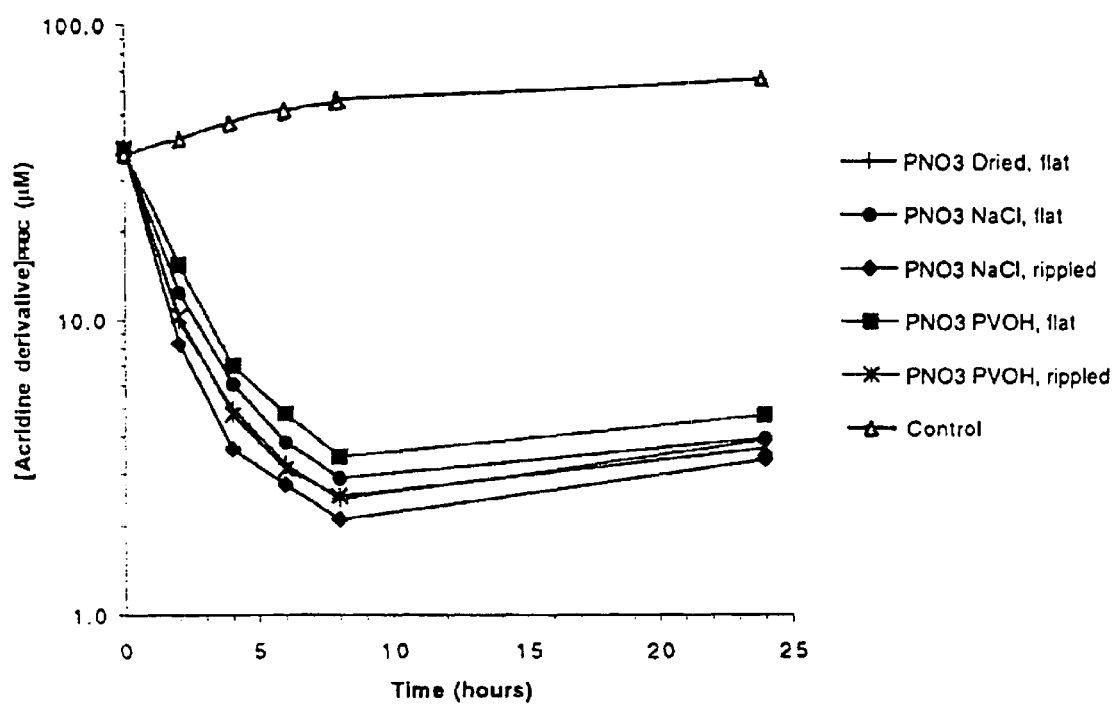
FIG. 26 is a graph showing the sorption of an acridine derivative in packed RBC by a membrane made in accordance with the present invention.

Next, the cooled containers were allowed to come to room temperature. Twenty (20) ml of a 30 mM glutathione solution in 4.1% dextrose was introduced into a pouch containing approximately 30 mg of an acridine compound [N,N-bis (2-chloroethyl)]-2-aminoethyl 3 [(Acridinyl-3-yl) amino] proprionate dihydrochloride. The powder was dissolved and the solution was added to the packed red blood cells and mixed to obtain final concentrations in the packed red blood cells of approximately 200 µM of the acridine compound and 2 mM of L-glutathione. After transfer to a secondary container, the dosed packed red blood cells were held in a static condition at room temperature for approximately 8 hours.

after transfer to the container including the membrane. Samples were prepared for HPLC analysis to determine concentrations of the acridine derivative 5-[(β-carboxyethyl) amino] acridine (abbreviated as AD) and total L-glutathione (oxidized (GSH) and reduced (GSSH)). Samples were also analyzed for % hematocrit, % hemolysis, hemoglobin, ATP concentration, pH and potassium (K+ leakage). Samples were also collected and analyzed after one and two week exposure to the membrane at 4° C. The results after 8 hours exposure to the membrane are summarized in Table 2 and also in FIGS. 26–28. The results after 1 week and 2 week exposure the membrane are summarized in Tables 4 and 5.

TABLE 3

SUMMARY OF RESULTS AFTER 8 HOURS EXPOSURE TO MEMBRANE

| Unit No. | Condition | Residual [AD] (µM) | Residual [GSH] and [GSSH] (mM) | % Lysis t=0 hr | % Lysis t=8 hr | [K+] (mmol/L) | % HCT | [ATP] (µmol/g Hb) t=8 hr | pH |
|---|---|---|---|---|---|---|---|---|---|
| 1 | PNO3 Dried, flat | 2.45 | 3.32 | 0.05 | 0.26 | 5.17 | 67 | 4.67 | 6.74 |
| 2 | PNO3 NaCl, flat | 2.89 | 2.54 | 0.05 | 0.29 | 4.64 | 63 | 4.68 | 6.76 |
| 3 | PNO3 NaCl, rippled | 2.10 | 2.66 | 0.06 | 0.19 | 4.72 | 63 | 4.65 | 6.77 |
| 4 | PNO3 PVOH, flat | 3.39 | 2.82 | 0.04 | 0.46 | 5.40 | 67 | 4.66 | 6.75 |
| 5 | PNO3 PVOH, rippled | 2.52 | 1.80 | 0.05 | 0.31 | 5.22 | 66 | 4.68 | 6.75 |
| 6 | Control | 54.98 | 6.13 | 0.06 | 0.06 | 4.77 | 64 | 4.64 | 6.74 |

TABLE 4

SUMMARY OF RESULTS AFTER 1 WEEK EXPOSURE TO MEMBRANE

| Unit No. | Condition | Residual [AD] (µM) | Residual [GSH] and [GSSH] (mM) | % Lysis | [K+] (mmol/L) | % HCT | [ATP] (µmol/g Hb) | pH |
|---|---|---|---|---|---|---|---|---|
| 1 | PNO3 Dried, flat | 3.99 | 0.33 | 0.31 | 17.10 | 66 | 4.35 | 6.54 |
| 2 | PNO3 NaCl, flat | 3.89 | 0.35 | 0.40 | 15.68 | 62 | 4.36 | 6.55 |
| 3 | PNO3 NaCl, rippled | 2.93 | 0.46 | 0.26 | 15.90 | 63 | 4.33 | 6.53 |
| 4 | PNO3 PVOH, flat | 3.61 | 0.35 | 0.52 | 16.80 | 65 | 4.31 | 6.56 |
| 5 | PNO3 PVOH, rippled | 3.13 | 0.44 | 0.42 | 17.32 | 65 | 4.27 | 6.58 |
| 6 | Control | 70.90 | 4.12 | 0.11 | 16.52 | 63 | 4.82 | 6.49 |

TABLE 5

SUMMARY OF RESULTS AFTER 2 WEEKS EXPOSURE TO MEMBRANE

| Unit No. | Condition | Residual [AD] (µM) | Residual [GSH] and [GSSH] (mM) | % Lysis | [K+] (mmol/L) | % HCT | [ATP] (µmol/g Hb) | pH |
|---|---|---|---|---|---|---|---|---|
| 1 | PNO3 Dried, flat | 4.08 | 0.41 | 0.33 | 27.83 | 64 | 3.48 | 6.35 |
| 2 | PNO3 NaCl, flat | 4.23 | 0.39 | 0.39 | 24.63 | 62 | 3.52 | 6.35 |
| 3 | PNO3 NaCl, rippled | 3.09 | 0.50 | 0.27 | 25.65 | 62 | 3.60 | 6.35 |
| 4 | PNO3 PVOH, flat | 4.21 | 0.40 | 0.50 | 26.58 | 63 | 3.53 | 6.36 |
| 5 | PNO3 PVOH, rippled | 3.38 | 0.41 | 0.39 | 27.42 | 65 | 3.52 | 6.35 |
| 6 | Control | 80.58 | 3.94 | 0.09 | 26.49 | 63 | 3.47 | 6.33 |

Figure 27:
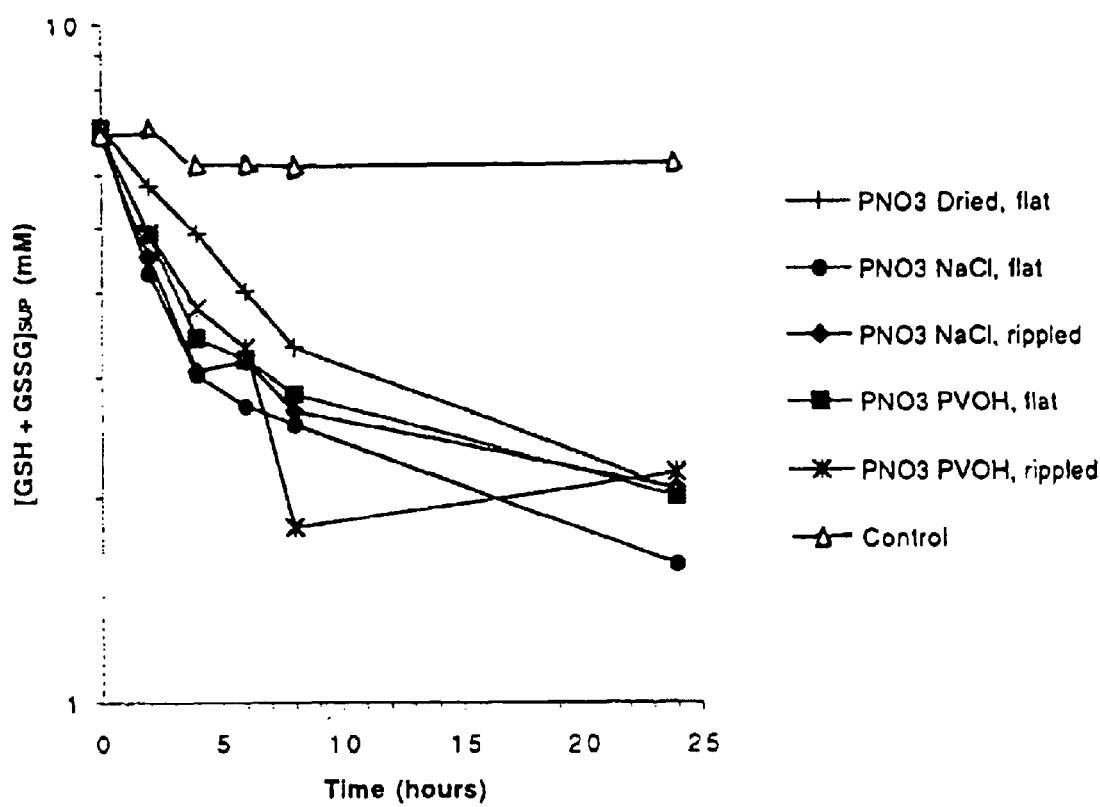
FIG. 27 is a graph showing the sorption of L-glutathione in packed RBC by a membrane made in accordance with the present invention.

Following the 8 hour incubation period, the treated packed red blood cells were sterile connected to a container including the membranes made as described above. The containers with packed red blood cells and the membranes were placed on an orbital shaker (72 cycle/minute) at room temperature for 8 hours. After 8 hours, the units were transferred to 4° C. storage where they were agitated once every 4 hours for a 2 minute duration on a platelet shaker. A sample was collected every 2 hours for the first 8 hours As shown from foregoing and in FIG. 26, substantial sorption of the acridine derivatives was obtained in under 5 hours. Substantial sorption of L-glutathione (oxidized and reduced) was also achieved in under 24 hours (FIG. 27). Hemolysis and ATP levels remained acceptable for transfusion of RBCs to recipients (FIG. 28).

The present invention has been described, for purposes of illustration only, in the context of selected embodiments and methods. It will be appreciated, however, that various modifications of the embodiments and methods described herein are possible in accordance with the scope of the appended claims.

That which is claimed:

1. A flexible, composite sheet membrane comprising:
    a polymeric support, said support having a first side and a second side, wherein each of said first and second sides comprises a coating of a non-fiberized polymeric material,
    said material comprising a particulate blended with a polymer, said particulate being substantially physically immobilized by said polymer,
    each of said sides having a coating of said material substantially equal in thickness and wherein the outer surface of said membrane has a porous and selectively permeable skin, and wherein less of said particulate is disposed at said outer surface than is disposed further in the interior of said membrane.

2. The membrane of claim 1 wherein the majority of said particles have a diameter less than about 20 μm.

3. The membrane of claim 1 wherein said membrane comprises a contoured sheet.

4. The membrane of claim 3 wherein said membrane comprises a rippled sheet.

5. The membrane of claim 3 wherein said membrane comprises a pleated sheet.

6. The membrane of claim 1 further comprising a coating of hydrophilizing agent.

7. The membrane of claim 1 wherein said polymer is selected from the group consisting of polyurethane, polyvinylidenefluoride, cellulose acetate, polyvinyl chloride and ethylene vinyl alcohol copolymer.

8. The membrane of claim 1 comprising between about 5% and 30% of said polymeric material.

9. The membrane of claim 1 comprising about 70% by weight of said particulate material.

10. The membrane of claim 1 wherein said support comprises a polyester mesh material.

11. A flexible, composite sheet membrane comprising:
    a polymeric support, said support comprising a first side and a second side,
    at least one of said first or second sides comprising a first coating of a particulate blended with a polymer, said particulate being substantially physically immobilized by said polymer, wherein less of said particulate is disposed near said skin than is disposed in the interior of said membrane and
    a second coating of a hydrophilizing agent.

12. The membrane of claim 11 wherein the majority of said particles have a diameter less than about 20 μm.

13. The membrane of claim 11 wherein said membrane comprises a contoured sheet.

14. The membrane of claim 13 wherein said membrane comprises a rippled sheet.

15. The membrane of claim 13 wherein said membrane comprises a pleated sheet.

16. The membrane of claim 11 wherein said polymer is selected from the group consisting of polyurethane, polyvinylidenefluoride, cellulose acetate, polyvinyl chloride and ethylene vinyl alcohol copolymer.

17. The membrane of claim 11 comprising between about 5% and 30% of said polymeric material.

18. The membrane of claim 11 comprising about 70% by weight of said particulate material.

19. The membrane of claim 11 wherein said support comprises a polyester mesh material.

20. A flexible, composite membrane comprising:
    a polymeric support, said support comprising a first side and a second side;
    at least one of said first or second sides comprising a first coating of a particulate blended with a polymer,
    said particulate being substantially physically immobilized by said polymer, wherein less of said particulate is disposed near said skin than is disposed in the interior of said membrane.

21. The membrane of claim 20 wherein said polymer is selected from the group consisting of polyurethane, polyvinylidenefluoride, cellulose acetate, polyvinyl chloride and ethylene vinyl alcohol copolymer.

22. The membrane of claim 20 comprising between about 5% and 30% of said polymeric material.

23. The membrane of claim 20 comprising about 70% by weight of said particulate.

* * * * *